US008932223B2

(12) United States Patent
Emelianov et al.

(10) Patent No.: US 8,932,223 B2
(45) Date of Patent: Jan. 13, 2015

(54) CATHETER FOR INTRAVASCULAR ULTRASOUND AND PHOTOACOUSTIC IMAGING

(75) Inventors: Stanislav Emelianov, Austin, TX (US); Andrei Karpiouk, Austin, TX (US); Bo Wang, Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 13/505,345

(22) PCT Filed: Nov. 1, 2010

(86) PCT No.: PCT/US2010/055006
§ 371 (c)(1),
(2), (4) Date: Jul. 10, 2012

(87) PCT Pub. No.: WO2011/053931
PCT Pub. Date: May 5, 2011

(65) Prior Publication Data
US 2012/0271170 A1    Oct. 25, 2012

Related U.S. Application Data

(60) Provisional application No. 61/257,390, filed on Nov. 2, 2009.

(51) Int. Cl.
*A61B 8/00* (2006.01)
*A61B 8/12* (2006.01)
*A61B 5/00* (2006.01)
*A61B 8/08* (2006.01)

(52) U.S. Cl.
CPC ............... *A61B 8/12* (2013.01); *A61B 5/0095* (2013.01); *A61B 8/0891* (2013.01); *A61B 8/485* (2013.01)
USPC ........... 600/439; 600/407; 600/437; 600/459; 600/466; 600/467; 600/473; 600/474; 600/475; 600/476

(58) Field of Classification Search
USPC ......... 600/407, 437, 439, 459, 462, 466–467, 600/473–476
See application file for complete search history.

(56) References Cited

U.S. PATENT DOCUMENTS 5,115,814 A * 5/1992 Griffith et al. ................ 600/463
5,161,531 A * 11/1992 Parsons et al. ................ 600/342
(Continued)

FOREIGN PATENT DOCUMENTS

WO    2006061829    6/2006
WO    2010080776    7/2010
(Continued)

OTHER PUBLICATIONS

Shah, et al., "Temperature Monitoring Using Ultrasound and Photoacoustic Imaging During Laser Therapy", Abstract of the 25th Annual Houston Conference on Biomedical Engineering Research, The Houston Society for Engineering in Medicine and Biology, 53 (2008).

(Continued)

*Primary Examiner* — Peter Luong
(74) *Attorney, Agent, or Firm* — Parker Highlander PLLC

(57) ABSTRACT

A design and a fabrication method for an intravascular imaging and therapeutic catheters for combined ultrasound, photoacoustic, and elasticity imaging and for optical and/or acoustic therapy of hollow organs and diseased blood vessels and tissues are disclosed in the present invention. The invention comprises both a device—optical fiber-based intravascular catheter designs for combined IVUS/IVPA, and elasticity imaging and for acoustic and/or optical therapy—and a method of combined ultrasound, photoacoustic, and elasticity imaging and optical and/or acoustic therapy. The designs of the catheters are based on single-element catheter-based ultrasound transducers or on ultrasound array-based units coupled with optical fiber, fiber bundles or a combination thereof with specially designed light delivery systems. One approach uses the side fire fiber, similar to the one utilized for biomedical optical spectroscopy. The second catheter design uses the micro-optics in the manner of a probe for optical coherent tomography.

44 Claims, 11 Drawing Sheets

(56) References Cited

U.S. PATENT DOCUMENTS

| | | | | |
|---|---|---|---|---|
| 5,217,018 | A | * | 6/1993 | Dias .............................. 600/463 |
| 5,873,828 | A | * | 2/1999 | Fujio et al. .................... 600/439 |
| 7,697,275 | B2 | | 4/2010 | Chen et al. |
| 7,711,403 | B2 | | 5/2010 | Jay et al. |
| 7,711,413 | B2 | | 5/2010 | Feldman et al. |
| 2003/0220556 | A1 | * | 11/2003 | Porat et al. .................... 600/407 |
| 2007/0291275 | A1 | | 12/2007 | Diamond |
| 2008/0221647 | A1 | | 9/2008 | Chamberland et al. |
| 2008/0228073 | A1 | | 9/2008 | Silverman et al. |
| 2009/0299195 | A1 | * | 12/2009 | Muller et al. ................. 600/466 |

FOREIGN PATENT DOCUMENTS

| | | |
|---|---|---|
| WO | 2010080776 A1 | 7/2010 |
| WO | 2011053931 | 5/2011 |

OTHER PUBLICATIONS

International Search Report and Written Opinion for PCT/US2010/055006 dated Jun. 23, 2011.
International Preliminary Report on Patentability for PCT/US2010/055006 dated May 8, 2012.
Aglyamov, et al., "Model-Based Reconstructive Elasticity Imaging Using Ultrasound," International Journal of Biomedical Imaging, 2007; Article ID 35830, 11 pages.
ANSI. American National Standard for Safe Use of Lasers, vol. Z136.1-2007. New York, USA: American National Standards Institute, 252 pp.
Beard, PC, et al, "Characterization of Post Mortem Arterial Tissue Using Time-Resolved Photoacoustic Spectroscopy at 436,461 and 532 nm," Phy. Med. Biol., 1997; 42:177-198.
Beard, et al., "Optical Fiber Photoacoustic—Photothermal Probe," Optics Letters, 1998; 23(15):1235-1237.
Berlis, et al., "Mechanical Thrombolysis in Acute Ischemic Stroke with Endovascular Photoacoustic Recanalization," Stroke, 2004; 35:1112-1116.
Cheong, et al., "A Review of the Optical Properties of Biological Tissues," IEEE Journal of Quantum Electronics, 1990; 26(12):2166-2185.
Compton, et al., "Genetically Defined Therapy of Inherited Long-QT Syndrome Correction of Abnormal Repolarization by Potassium," Circulation, 1996; 94:1018-1022.
D'Hooge, et al., "Regional Strain and Strain Rate Measurements by Cardiac Ultrasound: Principles, Implementation and Limitations," Eur J Echocardiography, 2000; 1:154-170.
De Korte, et al., "Identification of Atherosclerotic Plaque Components with Intravascular Ultrasound Elastography In Vivo: A Yucatan Pig Study," Circulation, 2002; 105:1627-1630.
De Korte, et al., Intravascular Ultrasound Elastrography: Assessment and Imaging of Elastic Properties of Diseased Arteries and Vulnerable Plaque, European Journal of Ultrasound, 1998; 7:219-224.
Faber, et al., "Oxygen Saturation-Dependent Absorption and Scattering of Blood," Physical Review Letters, 2004; 93 (2):028102.
Fomitchov, et al., "Photoacoustic Probes for Nondestructive Testing and Biomedical Applications," Applied Optics, 2002; 41(22):4451-4459.
Fujimoto, et al., "High Resolution in Vivo Intra-Arterial Imaging with Optical Coherence Tomography," Heart, 1999; 82:128-133.
Gao, et al., "Imaging of the Elastic Properties of Tissue—A Review," Ultrasound in Medicine and Biology, 1996; 22 (8):959-977.
Henrichs, et al., "Atherosclerotic Plaque Characterization with Optoacoustic Imaging," Proceedings of SPIE, 2005; 5697:217-223.
Hollman, et al., Strain Imaging of Corneal Tissue with an Ultrasound Elasticity Microscope, Cornea, 2002; 21 (1):68-73.
Jin, et al., "Imaging of High-Intensity Focused Ultrasound-Induced Lesions in Soft Biological Tissue Using Thermoacoustic Tomography," Med. Phys., 2005; 32(1):5-11.
Levinson, et al "Sonoelastic Determination of Human Skeletal Muscle Elasticity," J. Biomechanics, 1995; 28 (10):1145-1154.

Madsen, et al., "Ultrasound Focal Lesion Detectability Phantoms," Med. Phys., 1991; 18(6):1171-1181.
Mitic, et al., "Time-Gated Transillumination of Biological Tissues and Tissuelike Phantoms," Applied Optics, 1994; 33 (28):6699-6710.
Naghavi, et al., "From Vulnerable Plaque to Vulnerable Patient A Call for New Definitions and Risk Assessment Strategies: Part I," Circulation, 2003; 108:1664-1672.
Nissen, et al., "Intravascular Ultrasound: Novel Pathophysiological Insights and Current Clinical Applications," Circulation, 2001; 103:604-616.
Ophir, et al., "Elastography: Imaging the Elastic Properties of Soft Tissues with Ultrasound," J Med Ultrasonics, 2002; 29:155-171.
Ophir, et al., "Elastography: Ultrasonic Imaging of Tissue Strain and Elastic Modulus in Vivo," European Journal of Ultrasound, 3, 1996; pp. 49-70.
Parker, et al., "Techniques for Elastic Imaging: A Review," IEEE Engineering in Medicine and Biology Magazine, 1996; 15:52-59.
Patel, et al., "Pulsed Optoacoustic Spectroscopy of Condensed Matter," Reviews of Modern Physics, 1981; 53 (3):517-550.
Petrov, et al., "Multiwavelength Optoacoustic System for Noninvasive Monitoring of Cerebral Venous Oxygenation: A Pilot Clinical Test in the Internal Jugular Vein," Optics Letters, 2006; 31(12):1827-1829.
Pilatou, et al., "Analysis of Three-Dimensional Photoacoustic Imaging of a Vascular Tree in Vitro," Review of Scientific Instruments, 2003; 74(10):4495-4499.
Pogue, et al., "Review of Tissue Simulating Phantoms for Optical Spectroscopy, Imaging and Dosimetry," Journal of Biomedical Optics, 2006; 11(4):041102.
Prahl, Scott, Oregon Medical Laser Center, see at http://omlc.ogi.edu/spectra/hemoglobin/summary.html (2000).
Schwarzacher, et al., "Clinical Use of Intravascular Ultrasound," Seminars in Interventional Cardiology, 1997; 2:1-9.
Sethuraman, et al., "Remote Temperature Estimation in Intravascular Photoacoustic Imaging," Ultrasound in Medicine & Biology, 2008; 34(2):299-308.
Sethuraman, et al., "Ex Vivo Characterization of Atherosclerosis Using Intravascular Photoacoustic Imaging," Optics Express, Dec. 10, 2007; 15(25):16657-16666.
Sethuraman, et al., "Intravascular Photoacoustic Imaging Using an IVUS Imaging Catheter," IEEE Transactions on Ultrasonics, Ferroelectrics, and Frequency Control, May 2007; 54(5):978-986.
Sethuraman, et al., "Spectroscopic Intravascular Photoacoustic Imaging to Differentiate Atherosclerotic Plaques," Optics Express, Mar. 3, 2008; 16(5): Optics Expres 3362-3367.
Shah, et al., "Ultrasound Imaging to Monitor Photothermal Therapy—Feasibility Study" Optics Express, Mar. 17, 2008; 16(6):3776-3785.
Shah, et al., "Ultrasound Guidance and Monitoring of Laser-Based Fat Removal," Lasers in Surgery and Medicine, 2008; 40:680-687.
Shah, et al., "Photoacoustic and Ultrasound Imaging to Guide Photothermal Therapy: Ex Vivo Study," Proc. of SPIE, 2008; 6856, 68560U:1-7.
Shah, et al., "Photoacoustic Imaging and Temperature and Measurement for Photothermal Cancer Therapy," Journal of Biomedical Optics, May/Jun. 2008; 13(3):034024.
Shah, et al., "Real-Time Photoacoustic and Ultrasound Imaging to Monitor Photothermal Therapy in Mice," Abstract and Presentation at the 2009 SPIE Photonics West Symposium: Photons Plus Ultrasound: Imaging and Sensing, 2009, 1 page.
Shapo, et al., "Displacement and Strain Imaging of Coronary Arteries with Intraluminal Ultrasound," IEEE Transactions on Ultrasonics, Ferroelectrics, and Frequency Control, 1996; 43(2):234-246.
Stary, et al., "A Definition of Advanced Types of Atherosclerotic Lesions and a Histological Classification of Atherosclerosis," Arteriosclerosis, Thrombosis, and Vascular Biology, 1995; 15:1512-1531.
Tam, Andrew C., "Applications of Photoacoustic Sensing Techniques," Reviews of Modern Physics, Apr. 1986; 58 (2):381-431.
Utzinger, et al., "Fiber Optic Probes for Biomedical Optical Spectroscopy," Journal of Biomedical Optics, 2003; 8 (1):121-147.

(56) References Cited

OTHER PUBLICATIONS

Van Gemert, et al., "Optical Properties of Human Blood Vessel Wall and Plaque," Lasers in Surgery and Medicine, 1985; 5:235-262.

Viator, JA, et al., "Design and Testing of an Endoscopic Photoacoustic Probe for Determination of Treatment Depth After Photodynamic Therapy," Proceedings of SPIE, 2001; 4256:16-26.

Virmani, et al., "Lessons from Sudden Coronary Death: A Comprehensive Morphological Classification Scheme for Atherosclerotic Lesions," Arteriosclerosis, Thrombosis, and Vascular Biology, 2000; 20:1262-1275.

Waterworth, et al., "Optical Transmission Properties of Homogenised Milk Used as a Phantom Material in Visible Wavelength Imaging," Australasian Physical & Engineering Sciences in Medicine, 1995; 18(1):39-44.

Wygant, et al., Integrated Ultrasound Imaging Systems Based on Capacitive Micromachined Ultrasonic Transducer Arrays, IEEE in Sensors, 2005; pp. 704-707.

Zhang, et al., "Imaging of Hemoglobin Oxygen Saturation Variations in Single Vessels in Vivo Using Photoacoustic Microscopy," Applied Physics Letters, 2007; 90:053901.

* cited by examiner

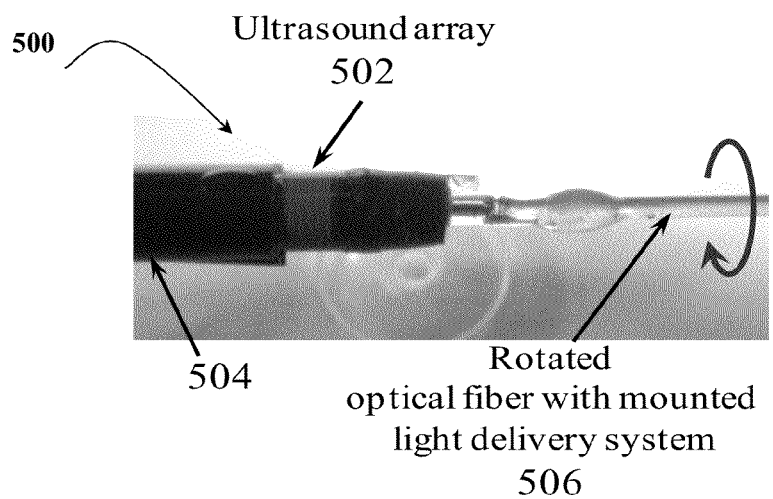
FIG. 5B
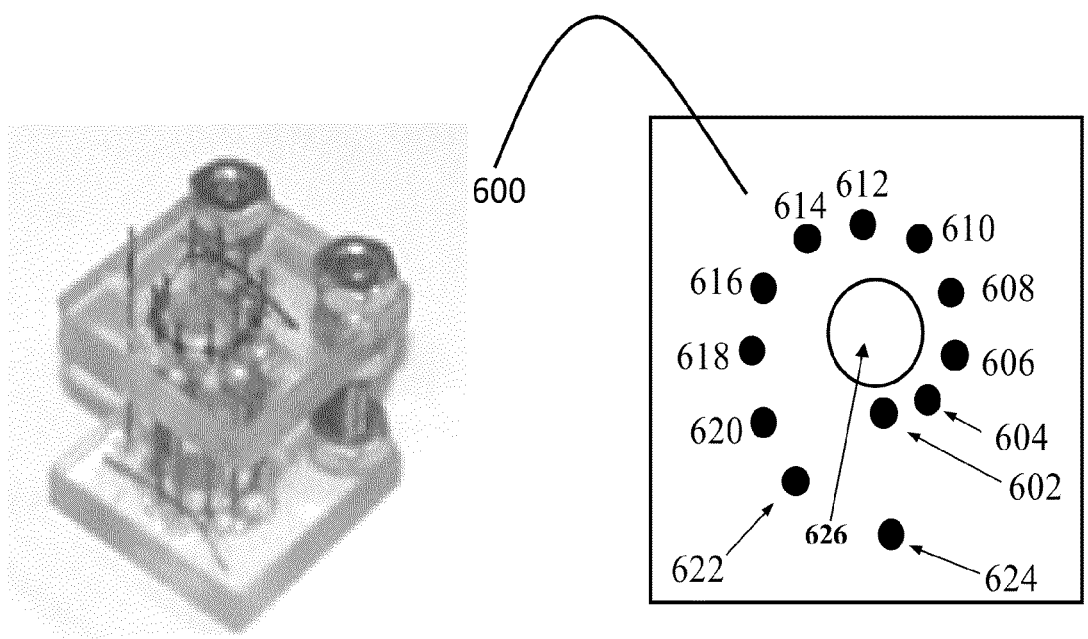
FIG. 6A
FIG. 6B

Ultrasound images

Photoacoustic images

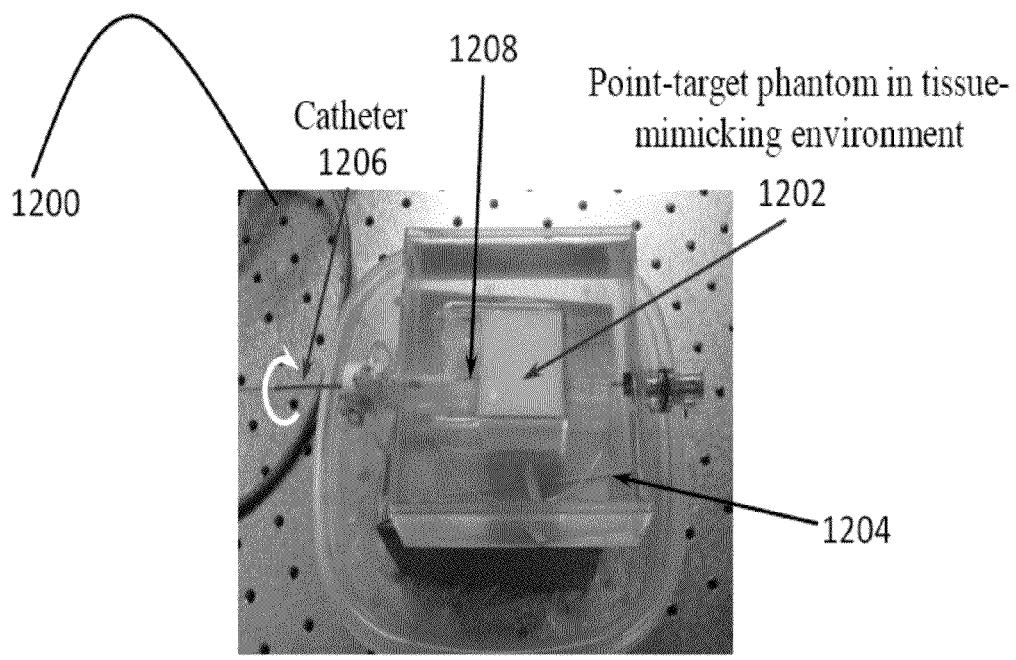
*FIG. 12A*
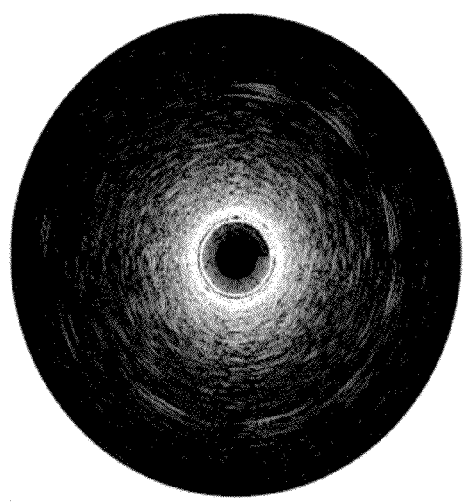 
*FIG. 12B*            *FIG. 12C*

CATHETER FOR INTRAVASCULAR ULTRASOUND AND PHOTOACOUSTIC IMAGING

CROSS-REFERENCE TO RELATED APPLICATIONS

This application is a National Stage of International Application No. PCT/US2010/055006, filed Nov. 1, 2010 which claims the benefit of U.S. Provisional Application No. 61/257,390, filed Nov. 2, 2009. The contents of each of which are incorporated by reference in their entirety.

TECHNICAL FIELD OF THE INVENTION

The present invention relates in general to the field of combined intravascular ultrasound, photoacoustic and elasticity imaging and intravascular radiation and/or acoustic therapy, and more particularly, to the design and fabrication of an intravascular catheter for combined intravascular ultrasound, photoacoustic and elasticity imaging and for intravascular radiation and/or acoustic therapy.

BACKGROUND ART

Without limiting the scope of the invention, its background is described in connection with the design and fabrication of an intravascular catheter that combines intravascular ultrasound, photoacoustic and elasticity imaging and is capable of intravascular radiation and/or acoustic therapy.

WIPO Patent Application No. WO/2010/080776 (Thornton, 2010) describes a catheter assembly for an intravascular ultrasound system that includes a catheter and an imaging core disposed in the catheter. The imaging core includes a rotatable driveshaft, at least one light source, and at least one transducer. The at least one light source is disposed at a distal end of the rotatable driveshaft. The at least one light source is configured and arranged for rotating with the driveshaft and also for transforming applied electrical signals to light for illuminating an object in proximity to the catheter. The at least one transducer is also disposed at the distal end of the rotatable driveshaft. The at least one transducer is configured and arranged for rotating with the driveshaft. The at least one transducer is configured and arranged for receiving acoustic signals generated by the object in response to illumination of the object by the light emitted from the at least one light source.

U.S. Pat. No. 7,711,413 issued to Feldman et al., (2010) relates to a catheter imaging probe for a patient. The probe of the Feldman patent includes a conduit through which energy is transmitted. The probe includes a first portion through which the conduit extends. The probe includes a second portion which rotates relative to the conduit to redirect the energy from the conduit. A method for imaging a patient. The method includes the steps of inserting a catheter into the patient. There is the step of rotating a second portion of the catheter relative to a conduit extending through a first portion of the catheter, which redirects the energy transmitted through the conduit to the patient and receives the energy reflected back to the second portion from the patient and redirects the reflected energy to the conduit.

Intravascular ultrasound (IVUS) imaging is widely used to image the atherosclerotic plaques in coronary arteries.[1-3] This invasive catheter-based approach is suitable to detect unrecognized disease, lesions of uncertain severity (40% to 75% stenosis), and risk of stratification of atherosclerotic lesions in interventional practice. Histopathalogical information, obtained from the IVUS, is not enough to characterize the plaques due to poor contrast between tissue's ultrasound properties, therefore an additional modality such as intravascular photoacoustic imaging (IVPA) must be used to assess the vulnerability of the plaques.

The IVPA imaging as a part of combined IVUS/IVPA imaging that was demonstrated by Sethuraman et al.[4] Photoacoustic imaging relies on contrast of light absorption constituents presented inside the arterial tissues and is based on an excitation of a tissue with shot laser pulses with consequent detection of acoustic transients, generated as a result of thermal expansion.[5-7] Currently, the photoacoustic imaging is successfully used in different biomedical areas.

The intravascular elasticity imaging as a part of the described intravascular imaging is used to image a distribution of shear elastic modulus in the artery.[8-11] The elasticity imaging relies on a stiffness contrast of artery tissues and plaques content and is based on obtaining several ultrasound images of the same cross-section of the artery during the deformation of the artery's wall under either externally applied force or as a result of normal cardiac cycles or a combination thereof. Using inverse problem formulations, the elasticity distribution is evaluated based on a distribution of the strain tensor components. The elasticity imaging approach is widely used in various clinical applications.[12-16]

Once pathology is detected and its vulnerability is assessed, the same integrated IVUS/IVPA imaging catheter can be used for thermal and/or radiation and/or acoustic therapy of the pathology. In such therapy, the absorbed light energy or acoustic energy or both is converted into a heat leading to necrosis of the pathology tissues. While the pulsed laser is coupled with the catheter to perform diagnostics imaging, the continuous wave (CW) source of a radiation, for instance, a CW laser, should be coupled with the catheter.[17-20] The laser is operated at a wavelength that is primarily absorbed by a typical pathology of the cells and molecules.

To enhance the radiation therapy effect, Shah et al. has proposed to use nanoparticles-based contrast agents.[19] Such contrast agents are conjugated with antibodies and can be injected into a blood vessel. After a certain time needed for contrast agents to reach the pathology and label the specific cells, the tissue is irradiated with CW laser light. The radiation is primarily absorbed by nanoparticles which cause heating. The heated nanoparticles lead to a temperature increase in the tissue environment thus inducing therapeutic effects.

In the acoustic therapy, a relatively low-frequency, high-intensity focused ultrasound (HIFU) beam is directed in the area of the detected pathology and, due to acoustic absorption, scattering and/or reflecting, leads to a temperature increase thus resulting in necrosis of the pathology tissues.[21,22] The HIFU treatment is also well-known modality of non-invasive therapy and can be performed either from outside or from the inside of the artery. However, to perform all of these imaging and therapy procedures clinically, specially designed catheters need to be used. Currently available catheters cannot be used both for combined IVUS, IVPA and elasticity imaging and for radiation and/or acoustic therapy.

The present invention describes two representative designs of fiber-based integrated catheters both for combined IVUS/IVPA imaging and for intravascular radiation and/or acoustic therapy. One design is based on single-element catheter-based ultrasound transducers coupled with specially designed light delivery systems. In this approach, the light delivery system is based on the side fire fiber, similar to that utilized for biomedical optical spectroscopy[23] or on the micro-optics in a manner of a probe for optical coherent tomography. In the second design, the integrated catheter is based on ultrasound array transducer that also is coupled with the side fire fiber or micro-optics light delivery system. In both types of the integrated catheters, the light delivery systems were designed to direct the light into the area or tissues imaged by the ultrasound transducer. In addition to that, the CW radiation utilized for radiation therapy is also delivered in the same area. Finally, an intravascular acoustic therapy can be performed using one or more ultrasound units that deliver the acoustic radiation in the desired area of the artery. Tunable in wide spectral range a Ns-pulsed laser-based system was employed as a light source for photoacoustic imaging, while ultrasound pulser/receiver was used for ultrasound imaging.

DISCLOSURE OF THE INVENTION

In one embodiment the present invention describes a device for intravascular ultrasound, photoacoustic and elasticity imaging or for intravascular radiation and/or acoustic therapy or for both comprising one or more intravascular ultrasound units comprising a proximal and a distal end and one or more optical units comprising a proximal end and a distal end combination. The ultrasound unit is comprised of one or more single-element ultrasound transducers, an array of ultrasound transducers or a combination of both. In one aspect one or more ultrasound units are used for imaging purposes transmitting ultrasound waves about the distal end of the catheter near orthogonally to the integrated catheter's longitudinal axis and to receiving both scattered and reflected into tissue ultrasound waves to reconstruct ultrasound images of artery's cross-section, to collect the consequences of ultrasound frames utilized for reconstruction a distribution of elastic properties of the artery's tissues and to detect ultrasound waves generated in tissue due to light-tissue interaction for reconstruction of photoacoustic images of the artery's cross-section or a combination of thereof. In another aspect the one or more ultrasound imaging and therapeutic units may rotate around a longitudinal axis of the catheter. In another aspect one or more of same ultrasound units are used for therapeutic purposes transmitting and focusing low-frequency high-power acoustic energy about the distal end of the catheter near orthogonally to the integrated catheter's longitudinal axis to irradiate the pathology leading to initiate tissue necrosis. In yet another aspect at least one ultrasound imaging and therapeutic unit is capable of transmitting an ultrasound wave about the distal end of the catheter at near right angles to the longitudinal axis of the catheter.

The optical unit is comprised of one or more optical fibers, optical fiber bundles or a combination of both and one or more light delivery systems mounted at the distal end of one or more optical fibers, optical bundles or combination of thereof. In one aspect one or more optical units are used for imaging purposes delivering the short pulses of radiation at desired spectral range into a lumen and emitting the light near orthogonally to the integrated catheter's longitudinal axis to generate ultrasound waves from tissues due to absorption of radiation and consequent thermal expansion of heated areas of arterial tissues. In one aspect the one or more optical units based on a single optical fiber, optical bundle or a combination thereof may rotate around a longitudinal axis of the catheter. In another aspect one or more optical units are used for therapeutic purposes delivering a high-power CW radiation or quasi CW radiation at desired spectral range about the distal end of the catheter near orthogonally to the integrated catheter's longitudinal axis to irradiate the pathology leading to tissue necrosis. A light-transparent tube comprising a sealed distal end and an open proximal end enclosed one or more optical unit's distal ends such that lumen content cannot reach the distal ends of the optical units. In one aspect, related to a side fire fiber-based catheter, the light transparent tube traps a medium such as gas enclosure to create a difference in the refractive index between the optical unit's material, and the gas was entrapped around the distal end of the optical fiber that was polished at a certain angle to redirect the light from the polished surface using total internal reflection effect. In another aspect, related to a micro-optic-based catheter, the distal end of the optical fiber is polished near orthogonally to the integrated catheter's longitudinal axis and emitted light is redirected at the desired angle by one or more optical elements such as micro-mirror, micro-prism, etc. or in any combinations, and a light-transparent tube traps a medium such as saline to avoid emitted radiation attenuation due to interaction with lumen content before light redirection. In both aspects, the light-transparent tube is also used to protect a patient from possible broken-off parts of the catheter. A fixture that is solid near distal end of the device and flexible along the integrated catheter is used to assemble the ultrasound units, optical units or both at the distal end to provide maximum overlap between one or more ultrasound beams emitted by one or ultrasound units and one or more light beams emitted by one or more optical units so the design of the fixture is suitable to concentrate the light in the area where the ultrasound waves propagate, to encapsulate the parts of the device to make integrated catheter round in cross-section, miniature and safe, and to be used as drive for cross-sectional and longitudinal scan of the vessel lumen.

In another embodiment the present invention describes an intravascular ultrasound, photoacoustic and elasticity imaging method. An intravascular ultrasound imaging is capable of reconstructing the distribution of ultrasound impedances in one imaged cross-section of artery or in several cross-sections of the artery. An ultrasound pulser/receiver operated in the pulse-echo mode is connected to the proximal end of the ultrasound imaging unit. An intravascular photoacoustic imaging is capable of reconstructing the distribution of optical absorption in the area of the artery where one or more ultrasound units of the catheter are directed to. A light source operated at one or more wavelengths capable of providing the best contrast between healthy tissues and plaque content or contrast agents or combination of both is connected to the proximal end of the one or more optical units. The light is emitted from the distal end of one or more optical units to irradiate the area of the artery where the one or more ultrasound imaging units are directed to, while the ultrasound pulsed/receiver is operated in echo mode detecting the ultrasound waves generated from the tissue as a result of thermal expansion after absorbing the electromagnetic waves. An elasticity imaging is capable of creating a distribution of shear modulus of the artery tissues and plaques in the imaged cross-section. The ultrasound pulser/receiver is operated in pulse-echo mode and several ultrasound images of the same cross-section of the artery are obtained while either external force is applied to the artery to initiate motions of the artery or the artery tissues are moved by during the cardiac cycles. The obtained frames can be converted into elasticity images.[24] For radiation therapy purposes, a CW light source operated at one or more wavelengths capable of interacting with plaque tissues or contrast agents is connected to the proximal end of one or more optical units. The distal end of the catheter is located and oriented such that the target is irradiated and light is concentrated fully or partially in the area of interest of the artery. The ultrasound pulser/receiver is operated in the pulse-echo mode to monitor the heating process ultrasonically. During the therapy process, one or more optical units and one or more ultrasound units that are not utilized for the therapy can be used for ultrasound, photoacoustic and elasticity imaging, separately or in combination thereof, to monitor the treated area of the artery.[25,26] For acoustic therapy purposes, one or more ultrasound units generate high-intensity ultrasound waves concentrated on the area under treatment.[21,22]

In one embodiment the present invention is an intravascular photoacoustic imaging and therapeutic catheter comprising: one or more intravascular ultrasound imaging and therapeutic units comprising a proximal end and a distal end, wherein the distal end comprises one or more single-element ultrasound transducers, one or more ultrasound arrays or a combinations thereof, wherein the proximal end comprises a port connecting at least one ultrasound unit to a pulser/receiver; one or more optical units comprising a proximal end and a distal end combination, wherein the distal end comprises one or more optical fibers, one or more optical bundles or a combination of both and one or more light delivery systems mounted on one or more optical fibers or one or more optical bundles or both, wherein the proximal end comprises a port to couple at least one optical unit to a pulsed light source and/or to couple at least one optical unit to a CW and/or long-pulse light source, an ultrasound pulser/receiver connected to the proximal end of the one or more ultrasound imaging and therapeutic units, a pulsed light source connected to the proximal end of the one or more optical units having a pulsed laser fluence, a CW light source connected to the proximal end of one or more optical units having a CW laser fluence, and an imager connected to the proximal end of the unit to capture one or more ultrasound, photoacoustic and elasticity images, wherein a majority of a laser and ultrasound energy is Omni-directionally directed at a target tissue and the imager is capable both of a distribution reconstruction of an ultrasound impedance, a shear elastic modulus and an optical absorption in an imaged target tissue cross-section and of performing an optical and/or an acoustic therapy. In one aspect the one or more optical units are incorporated longitudinally in or about the catheter. In another aspect the one or more ultrasound units are incorporated longitudinally in or about the catheter. In both aspects the integrated ultrasound and optical imaging and therapeutic device comprises one or more single-element ultrasound transducers, an ultrasound transducer array or a combination thereof and an optical fiber, an optical fiber bundle or a combination of thereof. In further aspects the integrated device may rotate around its longitudinal axis inside a lumen driven by one or multiple motors operated with the imager.

In one aspect at least one ultrasound imaging and therapeutic unit of the present invention is capable of transmitting an ultrasound wave about the distal end of the catheter and can irradiate an artery with pulsed ultrasound waves with consequent detection of the reflected and scattered ultrasound waves in a tissue. The one or more ultrasound imaging and therapeutic units can provide pulses of ultrasound waves with duration in a range of 1 nanosecond through 1 microsecond with a consequent detection of the ultrasound waves reflected and/or scattered from the tissues. In a specific aspect a central frequency of one or more ultrasound imaging and therapeutic units is chosen to provide a required resolution and a penetration depth to image the artery and nearby tissues and plaques. In another aspect the one or more ultrasound imaging and therapeutic units can irradiate the artery with a long pulse or CW ultrasound wave to provide a therapeutic effect. The central frequency of one or more ultrasound imaging and therapeutic units is chosen to provide an ultrasound wave capable of performing a therapy. The present invention allows for varying the duration of the pulses and a duty cycle of ultrasound waves as required for acoustic therapy.

The one or more optical units comprise one or more optical fibers, a fiber bundle or a combination thereof. The one or more optical units illuminate an area about the distal end of the catheter such that the emitted radiation overlaps with the ultrasound waves emitted by one or more ultrasound imaging and therapeutic units. In a further aspect the one or more optical units are designed to concentrate light in an area where the ultrasound waves propagate. In a specific aspect the proximal end of the one or more optical fibers or the fiber bundles comprises a polished flat tip near perpendicularly to the longitudinal axis of the catheter, wherein the tip is designed to be coupled with a light source. One or more ultrasound units and one or more optical units are mounted into a single device such that both ultrasound and optical radiations can penetrate non-obstructively and be aligned into the same space for maximum overlap with each other. The light delivery system in the present invention is mounted on the distal end of the one or more optical fibers or optical bundles or combination thereof In one aspect a light delivery system is based on micro-optics. The micro-optics is attached to the distal end of the one or more optical units. An optically transparent tube sealed on the distal end is mounted on the distal end of the one or more optical units as a separation between the micro-optics and imaged tissue. The tube is filled by a medium such as saline or water to reduce the radiation loss during light transmission. In another aspect a light delivery system utilizes the total internal effect. The distal end of optical fibers is polished at a certain angle to redirect light to almost near-right angle relative with respect of the longitudinal axis of the catheter. The optically transparent tube sealed on the distal end is mounted on one or more optical units hermetically to trap a medium such as gas near the distal end of optical units to create a difference in the refractive index between the optical unit's material and the entrapped medium. In both aspects the optically transparent tubes in both designs of the present invention is also mounted on the distal end of the one or more optical units to prevent mechanical damage of the artery. In one aspect the one or more optical units emits short pulsed light with a high fluence to perform a photoacoustic imaging. In another aspect the one or more optical units are capable of transmitting the CW or the long-pulse radiation to perform a light therapy.

In one aspect the pulsed laser is coupled with the proximal end of one or more optical units to irradiate the target tissue at one or more wavelengths, wherein the wavelengths of electromagnetic radiation are chosen to provide the best optical contrast. In another aspect of the device of the present invention the CW laser is coupled with proximal end of the one or more optical units to irradiate target tissues at one or more wavelengths. Both pulsed and CW laser sources can be coupled with same or different optical units as it is required for necessary procedure. In yet another aspect of the device of the present invention the imager is capable of providing the reconstructed distributions of ultrasound impedances, optical absorption and shear elastic modulus and of instructing a user to perform an acoustic and/or an optical therapy.

In another embodiment the present invention provides a method of imaging and treating a target tissue in a subject comprising the steps of: (i) identifying a subject in need of treatment of a target tissue using an intravascular imaging and therapeutic device capable of combined intravascular ultrasound, photoacoustic and elasticity imaging, (ii) irradiating the target tissue with radiation and/or ultrasound energy from an intravascular imaging and therapeutic device comprising: one or more intravascular ultrasound imaging and therapeutic units comprising a proximal end and a distal end, wherein the distal end comprises one or more single-element ultrasound transducers, one or more ultrasound arrays or a combinations thereof, wherein the proximal end comprises a port connecting at least one ultrasound unit to a pulser/reliever; one or more optical units comprising a proximal end and a distal end combination, wherein the distal end comprises one or more optical fibers, one or more optical bundles or a combination of both, wherein the proximal end comprises a port to couple at least one optical unit to a pulsed light source and/or to couple at least one optical unit to a continuous wave (CW) light source wherein a majority of a laser and ultrasound energy is Omni-directionally directed at a target tissue; an ultrasound pulser/receiver connected to the proximal end of the one or more ultrasound imaging and therapeutic units; a pulsed light source connected to the proximal end of the one or more optical units having a pulsed laser fluence; a CW light source connected to the proximal end of one or more optical units having a CW laser fluence; and an imager connected to the proximal end of the unit to capture one or more ultrasound, optical and elasticity images, and the imager is capable both of reconstruction of distributions of an ultrasound impedance, a shear elastic modulus and an optical absorption in an imaged target tissue cross-section and of performing a radiation and/or an acoustic therapy, (iii) reconstructing a distribution of an ultrasound impedance, a distribution of a shear elastic modulus and a distribution of an optical absorption in an imaged tissue cross-section or a combination of thereof, (iv) performing an acoustic and/or a radiation therapy of the target tissues, (v) performing the imaging and therapy all together or separately in any combinations thereof In one aspect of the method of the present invention related to imaging the distribution of the ultrasound impedance is reconstructed by transmitting of short ultrasound waves into the target tissue with consequent detection of reflected and scattered ultrasound waves. In another aspect of the method of the present invention the distribution of the optical absorption is reconstructed by transmitting of short light pulses into the target tissue with a consequent detection of ultrasound waves generated in the tissue due to thermal expansion by the irradiated light. In yet another aspect the distribution of shear elastic modulus is reconstructed by collecting of multiple ultrasound images where one or more strain tensor components are measured assessing local tissue's displacement in response to an external or a cardiac loading.

In one aspect of the method of the present invention related to the therapy the one or more ultrasound units irradiate an artery with long ultrasound pulses to perform an acoustic therapy of the artery. In another aspect the one or more optical units can irradiate tissues by CW or long light pulses to perform an optical therapy. In yet another aspect the optical and the acoustic therapy can be performed either simultaneously or separately. In a related aspect the reconstruction of the distributions and therapy can be performed either simultaneously or consequently, where ultrasound, photoacoustic and elasticity imaging can be performed during the therapy using optical and ultrasound units that are not engaged in therapy to guide and monitor the treatment. In a certain aspect the imager is capable of providing an imaging result or a therapy result in a format determined by a user.

DESCRIPTION OF THE DRAWINGS

For a more complete understanding of the features and advantages of the present invention, reference is now made to the detailed description of the invention along with the accompanying figures and in which:

FIG. 1A demonstrates the operation of the catheter. If total internal reflection (TIR) effect is reached for the light propagating along the fiber's axis, this light will be reflected from the polished surface (beam 1). Due to non-zero numerical aperture (NA) of the fiber and with the same β, TIR conditions are all the more valid for some portion of light propagating at the angle 0 to α in respect to the fiber axis (beam 2). However, under the same conditions, loses of the light are possible since TIR effect is not valid for portion of light propagating at the angle 0 to −α in respect to the fiber axis (beam 3), FIG. 1B is a photograph of the proximal end of the integrated IVUS/IVPA side fire fiber-based catheter utilizing the TIR effect, and FIG. 1C depicts an alignment between ultrasound and light beams;

FIG. 2A is a photograph of distal end of the mirror-based integrated IVUS/IVPA imaging catheter and FIG. 2B depicts an alignment of the ultrasound and light beams;

FIG. 3A shows a photograph of the view of the catheter and a magnified view of an ultrasound transducer and an outlet of light delivery system are shown and FIG. 3B is a schematic diagram of the catheter shown to clarify its construction;

FIGS. 5A and 5B show a distal end of a ultrasound array-based integrated IVUS/IVPA catheter with light delivery system that utilizes a single side fire fiber: FIG. 5A is a schematic diagram demonstrating a design wherein an ultrasound unit is an ultrasound array that is not rotated while the optical unit is a single optical fiber with installed light delivery system. The optical fiber is rotated inside the lumen and consequently irradiates parts of an artery that is been imaged by the ultrasound array, FIG. 5B shows a photograph of the prototype of the integrated IVUS/IVPA catheter based on an ultrasound array and light delivery system utilizing TIR effect;

FIG. 6A is a photograph and FIG. 6B is a diagram of the pencil rod-based phantom used in the IVUS/IVPA tissue-mimicking studies;

FIG. 8A is ultrasound, FIG. 8B is a photoacoustic image of the phantom without tissue-mimicking environment in water obtained using the side fire fiber-based integrated IVUS/IVPA catheter, FIG. 8C is ultrasound, and FIG. 8D is a photoacoustic image of the phantom without tissue-mimicking environment in water obtained using the mirror-based integrated IVUS/IVPA catheter;

FIG. 9A is ultrasound, FIG. 9B is a photoacoustic image of the phantom with tissue-mimicking environment in water obtained using the side fire fiber-based integrated IVUS/

IVPA catheter, FIG. 9C is ultrasound, and FIG. 9D is a photoacoustic image of the phantom with tissue-mimicking environment in water obtained using the mirror-based integrated IVUS/IVPA catheter;

FIG. 10A is ultrasound and FIG. 10B is a photoacoustic image of the phantom without tissue-mimicking environment in 20% solution of low-fat milk obtained using the side fire fiber-based integrated IVUS/IVPA catheter;

FIG. 11A is an ultrasound image and FIG. 11B is a photoacoustic image of the phantom with tissue-mimicking environment in water obtained using the mirror-based integrated IVUS/IVPA catheter. The catheter is realigned such that transducer is shifted two millimeters away from the mirror;

FIG. 12A demonstrates the experimental setup where the phantom in a plastic mold was stored in a water tank while the catheter is inserted into the phantom lumen and rotated within;

FIGS. 12B and 12C shows study images obtained by the rotatable side fire fiber-based integrated IVUS/IVPA catheter: FIG. 12B is an ultrasound, and FIG. 12C is a photoacoustic image of the phantom with tissue-mimicking environment obtained using the mirror-based integrated IVUS/IVPA catheter; FIG. 13A is ultrasound and FIG. 13B is a photoacoustic image of the phantom without tissue-mimicking environment in water obtained using the ultrasound array-based integrated IVUS/IVPA catheter with side fire fiber-based light delivery system irradiating the one pencil rod.

DESCRIPTION OF THE INVENTION

Figure 1A:
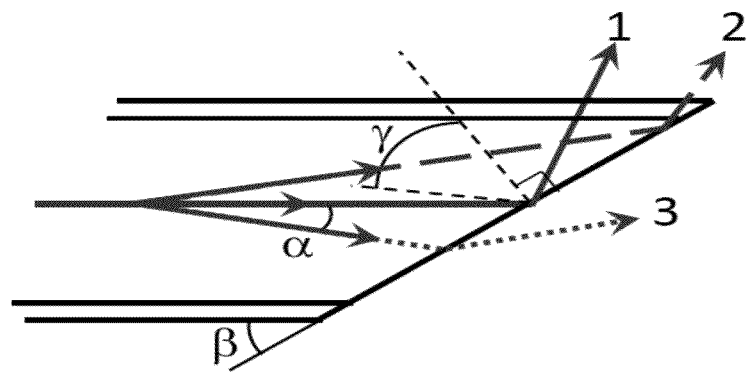
FIGS. 1A-1C are representations of the side fire fiber-based integrated IVUS/IVPA imaging catheter.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "photoacoustic or optoacoustic imaging" as used herein applies to any imaging method in which an electromagnetic radiation generates a detectable pressure wave or sound from which an image is calculated. As used herein, the term "intravascular" refers to within a blood vessel (for example, an artery, vein or capillary).

As used herein the term "catheter" broadly encompasses a wide array of devices for accessing remote locations, particularly within interior bodily vessels and cavities. Medical catheters may be used for tissue sampling, temperature measurements, drug administration or electrical stimulation to a selected tissue. With fiber optics, they may carry light for visual inspection of tissues. Medical catheters are generally maneuverable through anatomical cavities, vessels, and other structures of the body.

The term "optical fiber" as used herein is generally understood to refer to a light wave guide which, in its simplest form, consists of at least two layers of glass. One layer forms the core of the fiber and the other forms the fiber cladding and is placed round the core, whilst having a refractive index below that of the core.

The term "transducer array" as used herein refers to a series made up of a plurality of ultrasonic transducers, preferably situated directly adjacent to one another. The individual transducers are preferably positioned in alignment and generate, for example, flat or cylindrical ultrasonic waves. However, the transducer array may also be designed in such a way that spherical, ellipsoidal or otherwise curved wave fronts are generated.

The term "laser fluence" as used in the specification is a unit indicating the energy density of laser-light, which is obtained by integrating the energy amount per unit area by time. To be more specific, the "laser fluence" is an average intensity of laser light measured at a laser source or in an irradiation region.

The term "total internal reflection" refers to the reflection that occurs within a substance because the angle of incidence of light striking a boundary surface is in excess of the critical angle. The term "angle of incidence" refers to the angle formed between a ray of light striking a surface and the normal to the surface at the point of incidence. A "light ray" or "ray of light" is one of the radii of a wave of light that indicates the direction of light travel.

The term "image" as used herein broadly refers to any multidimensional representation, whether in tangible or otherwise perceptible form or in a computer memory or a storage medium, whereby a value of some characteristic is associated with each of a plurality of locations corresponding to dimensional coordinates of an object in physical space, though not necessarily mapped one-to-one thereonto. The term "image" also includes an ordered representation of detector signals corresponding to spatial positions. For example, the image may be an array of values within an electronic memory or holographic medium, or, alternatively, a visual image may be formed on a display device such as a video screen or printer. Thus, for example, the graphic display of the spatial distribution of some feature, such as atomic number, in one or more colors constitutes an image. Similarly, "imaging" refers to the rendering of a stated physical characteristic in terms of one or more images.

The term "proximal end" is considered to be the end closest to an operator, while the term "distal end" indicates the end of the device farthest from the operator.

The term "micro-optics" includes fine structures causing refraction and/or diffraction, the structures having characteristic depths/heights and often also widths of typically a few micrometers, for example of 0.5 µm-200 µm, preferably of between 1 µm and about 50 µm or between 1 µm and about 30 µm. In other words, the characteristic profile depths and the profile widths are of the order of a few wavelengths up to a few tens of wavelengths for refractive optics and of about one wavelength up to a few wavelengths for diffractive optics.

The term "wavelength" as used herein refers to the actual physical length comprising one full period of electromagnetic oscillation of a light ray or light beam. The term "irradiation" is broadly defined herein to include any process for treating or exposing something to light or other radiant energy to create a relatively more visibly marked portion compared to surrounding portions.

The present invention describes two designs of an integrated intravascular ultrasound, photoacoustic (IVUS/IVPA) and elasticity imaging catheter capable both of combined intravascular ultrasound, photoacoustic, and elasticity imaging and of radiation and/or acoustic therapy on an artery and/or nearby tissues. Such catheter consists of one or more ultrasound units that are either a single element ultrasound transducer or an ultrasound array transducer or a combination thereof, and one or more optical units that comprise one or more optical fibers, one or more optical bundles or a combination thereof. A light delivery system is mounted on one or more optical units. The one or more ultrasound units and one or more optical units are assembled into a single device such that ultrasound and optical beams propagate orthogonally to the longitudinal axis of the catheter with maximum overlap with each other.

The elasticity imaging of an artery is performed by one or more ultrasound units and is based on an intravascular ultrasound imaging of the artery. The radiation therapy is performed by one or more optical units that are also utilized in intravascular photoacoustic imaging. The acoustic therapy is performed by one or more ultrasound units that are also utilized in both ultrasound and photoacoustic imaging. The radiation therapy is performed by one or more optical units that are also utilized in photoacoustic imaging. Therefore, if the integrated IVUS/IVPA catheter is capable of combined IVUS/IVPA imaging, then it is also capable both of an intravascular elasticity imaging and of radiation therapy. A detailed description of two designs of an integrated IVUS/IVPA imaging catheter is given below.

A side fire fiber-based and a mirror-based catheter both utilizing a single-element ultrasound transducer and a side fire fiber-based catheter utilizing and ultrasound array are described in the present invention. Commercially available ultrasound transducers are utilized for ultrasound imaging and detection of photoacoustic transients. Laser pulses are delivered by custom-designed optical system mounted on the distal tip of a single optical fiber combined with the ultrasound transducer or transducer array into a single device.

Cardiovascular diseases represent a significant clinical problem with more than a million deaths annually due to problems associated with the arteries. The most common reason of the mortality is the formation and development of atherosclerotic plaques on artery's walls. These plaques narrow the cross-section of the vessels thus obstructing the normal blood flow.[27] In addition, the vulnerability of the atherosclerotic plaques depends on their composition.[28,29] Therefore, a successful treatment of the disease can be achieved if the distribution and the vulnerability of the plaques are diagnosed reliably.

A number of imaging techniques can be applied for diagnostic and treatment of the plaques. IVUS imaging is used to image the atherosclerotic plaques in coronary arteries.[1-3] This invasive catheter-based approach can detect unrecognized disease, lesions of uncertain severity (40% to 75% stenosis), and risk of stratification of atherosclerotic lesions in interventional practice. However, histopathalogical information, obtained from the IVUS, is not enough to characterize the plaques due to poor contrast between tissue's ultrasound properties. To further assess the vulnerability of the plaques, the present inventors previously introduced IVPA imaging.

The photoacoustic imaging component of a combined IVUS/IVPA was demonstrated by Sethuraman et al.[4] A number of scientific groups use the photoacoustic technique successfully for various vascular medical applications.[30-35] Photoacoustic imaging relies on contrast of light absorption properties of the tissues and is based on an excitation of a tissue with laser pulses and with consequent detection of acoustic transients, generated as a result of thermal expansion.[5-7] The applicability of the combined IVUS/IVPA imaging to detect and differentiate atherosclerosis has already been demonstrated,[36,37] but a specially designed catheter is needed to use such imaging clinically.

For IVUS imaging, an ultrasound imaging unit—a single-element catheter-based ultrasound transducer[38] or an ultrasound array[39] is used clinically. To realize the IVPA imaging modality, an optical unit based on single optical fiber, optical fiber bundle or a combination thereof should be incorporated with the ultrasound imaging unit. The fiber-based imaging units have already been reported for photoacoustic[40] and ultrasound[41] imaging separately, however, the integrated IVUS/IVPA imaging device capable both of combined IVUS/IVPA and elasticity imaging and of radiation and/or acoustic therapy has not been realized. In addition, both reported designs are selectively sensitive to signals coming along an axis of the catheter while a selectivity to signals coming across the axis is required for clinical applications.[32]

In the present invention, two designs of integrated IVUS/IVPA imaging catheters for combined IVUS/IVPA imaging are described. Particularly, one design is based on single-element catheter-based ultrasound transducers incorporated longitudinally with a single optical fiber. In another design, an ultrasound array is incorporated with a fiber-based optical unit. In both designs, single optical fibers with a proximal end polished flat and perpendicularly to the optical axis of the fiber were used. The specially designed light delivery systems capable of redirecting light at near right angle related to the optical axis of the fiber were mounted on a distal end of the fiber. One design of the light delivery systems uses the side fire fiber, similar to that utilized for biomedical optical spectroscopy.[23] The second design uses the micro-optics like a probe for optical coherent tomography.[42] All designs of integrated IVUS/IVPA imaging catheters must have a port for guide wire which is not shown in prototypes.

The operation of side fire fiber shown schematically in FIG. 1A is based on the total internal reflection (TIR) effect. The critical angle γ of TIR is defined as:

$$\gamma = \arcsin\left(\frac{n_{med}}{n_{core}}\right), \quad (1)$$

where $n_{med}$ and $n_{core}$ are refraction coefficients of medium outside of a fiber and of a fiber's core. If β is an angle of fiber's polishing then TIR effect appears when $$\beta \leq 90 - \gamma \quad (2)$$

However, the Eq. (2) has to be corrected due to fiber's non-zero NA. A full cone angle 2α of light inside of a fiber is defined as:

$$2 \cdot \alpha = 2 \cdot \left[90 - \arcsin\left(\frac{n_{cl}}{n_{core}}\right)\right], \quad (3)$$

where $n_{cl}$ is a refraction coefficient of fiber's cladding.

Considering Eqs. (1-3), TIR effect appears when the polishing angle $\beta_0'$ obeys the condition:

$$\beta_0' \leq \beta + \alpha = 180 - \arcsin\left(\frac{n_{med}}{n_{core}}\right) - \arcsin\left(\frac{n_{cl}}{n_{core}}\right). \quad (4)$$

A decrease of $\beta$ results an evaluation of the TIR effect contribution up to 100% when $\beta$ reaches $\beta_0$:

$$\beta_0 \leq \beta - \alpha = \arcsin\left(\frac{n_{cl}}{n_{core}}\right) - \arcsin\left(\frac{n_{med}}{n_{core}}\right). \quad (5)$$

Since a near right-angle light rotation is required, the blood in a lumen has to be substituted by a gas near fiber's distal end. In the case of air, angles $\beta_0'$ and $\beta$ will comprise 62.25° and 31.03° respectively, so light can be redirected within angle of 0 to 62.06° fully and within 62.06° and 124.5° partially.

Figure 1B:
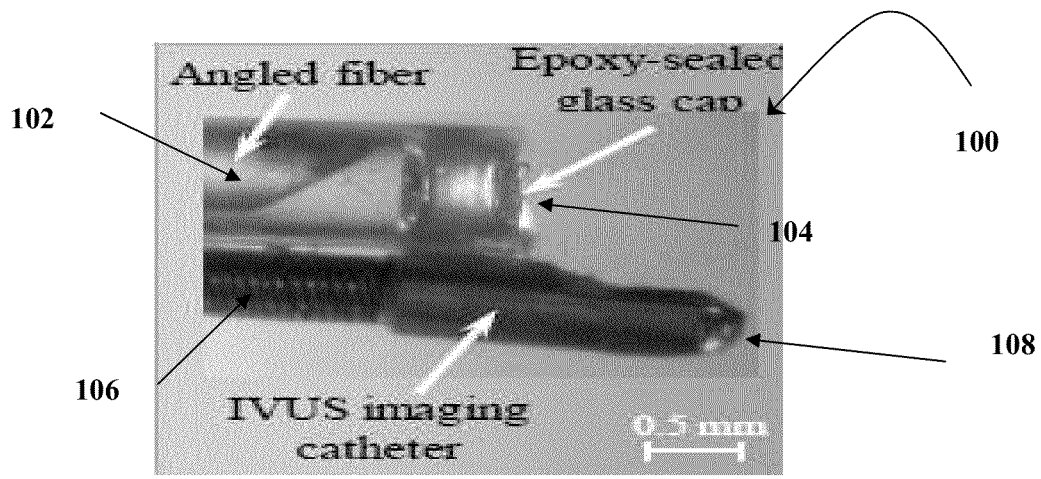
Figure 1C:
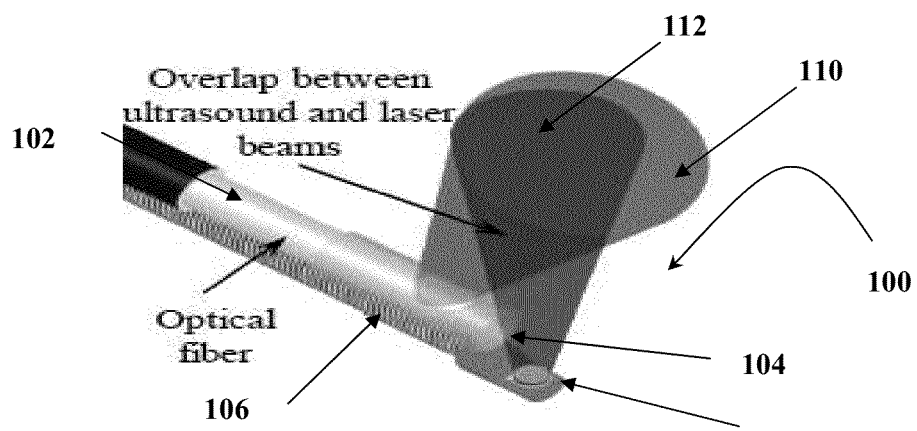

The photograph of a working prototype of the side fire fiber-based integrated IVUS/IVPA imaging catheter 100 and its schematic diagram are shown in FIGS. 1B and 1C, respectively. In this particular case, the distal end of the optical fiber 102 is polished at the angle of $\beta=33°$ and an air cup 104 is used as an air trapper near the distal end of the optical fiber 102. The ultrasound transducer 108 is on tube 106 and is fixed face to fiber 102 as it is shown in FIG. 1C using the shrinking tubing in a longitudinal position excluding direct interaction of ultrasound beam 112 with the light delivery system 102 and 104. The light divergence after the catheter was measured to be 26° while angle between light 110 and ultrasound beams 112 was 24°.

In the particular design of the micro-optic-based integrated IVUS/IVPA imaging catheter, the distal end of the optical fiber is polished flat and is perpendicular to the optical axis of the fiber, and a small mirror is used to rotate light. The mirror is attached to the fiber using a custom-made brass fixture comprising of a thin-wall cut along pipe and soldered to the pipe is a bended plate. Since this design does not rely on refraction coefficients of fiber's core and the medium, there is no need to have gas trapping cup near distal end of the light delivery system. However, the protective cup was installed on the distal end of the optical fiber to protect a patient from small sharp parts of the fiber if it would be broken accidentally as well as to make the distal end of the fiber round. To decrease the light losses, distilled water should fill the cup. The resulting angle between optical axis of the fiber and the plate with the glued mirror is chosen for better overlapping of light and ultrasound beams.

Figure 2A:
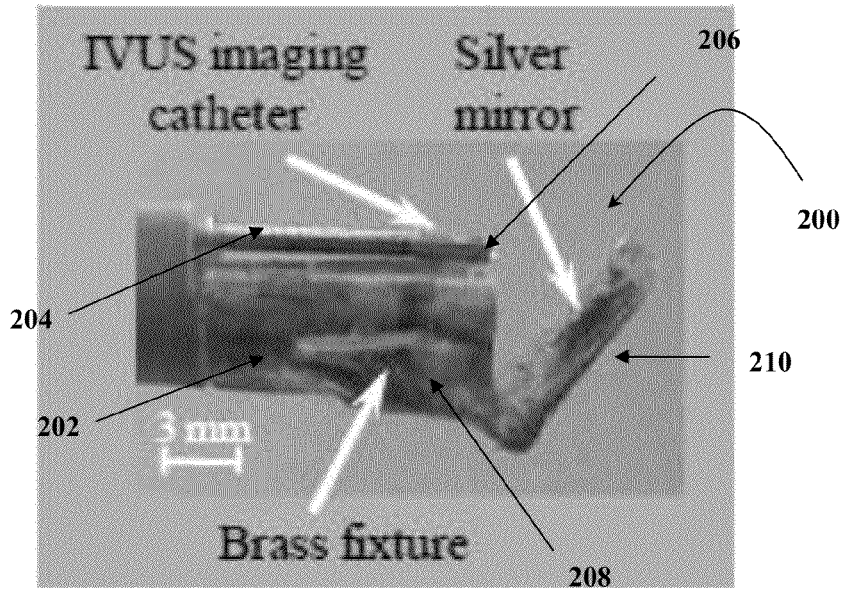
FIGS. 2A and 2B show a mirror-based integrated IVUS/IVPA catheter.
Figure 2B:
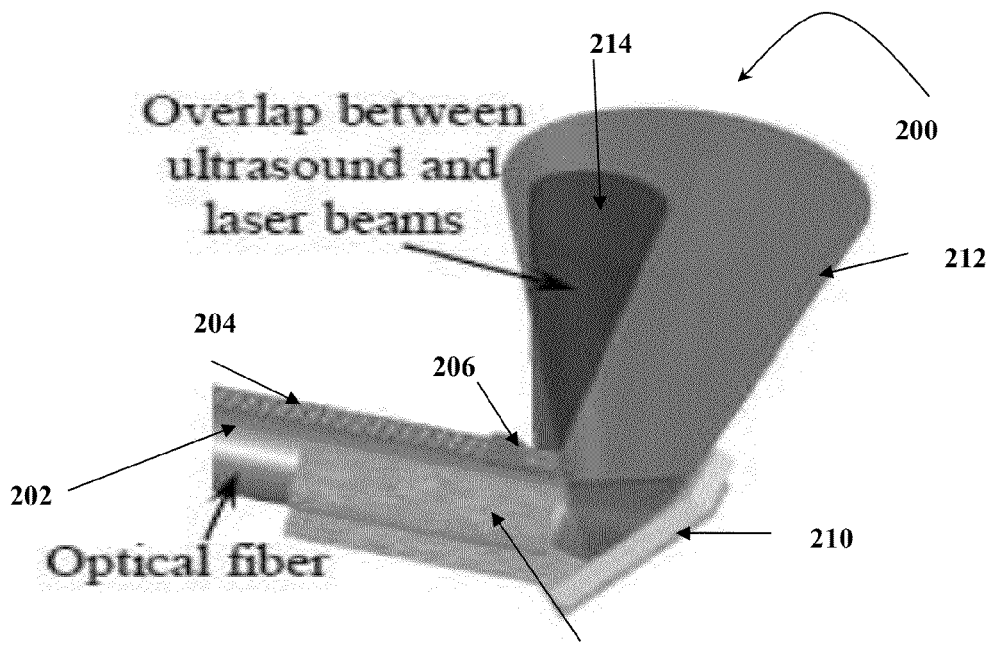

The photograph of mirror-based IVUS/IVPA catheter 200 and its schematic diagram are shown in FIG. 2A and FIG. 2B, respectively. The ultrasound transducer 206 was fixed face from fiber 202 using shrinking tubing 204 in the position resulted the maximum overlap of the ultrasound 214 and light beams 212. The angle between fiber's 202 optical axes and mirror 210 fixed with brass fixture 208 is approximately 52°. An angle between ultrasound and optical axes was estimated to be approximately 14°. Since the optical fiber 202 with NA of 0.39 and core refraction coefficient of 1.457 is located in water, the light divergence of the catheter comprises 17°.

A commercially available IVUS catheter (model Atlantis™SR plus, Boston Scientific SciMed, Inc.) based on a single-element ultrasound transducer with central frequency of 40 MHz was used.[38] An outer diameter of the catheter with a 500-μm-diam active element was 1 mm. Side fire fiber-based and mirror-based light delivery systems utilized single multimode optical fibers FT600EMT and FT1500EMT respectively (Thorlabs, Inc.). Laser threshold of silica core material is 1 MW/cm$^2$. Proximal ends of both fibers are polished regularly.

In side fire fiber-based light delivery system, the air cup was made out of quartz pipe with inner diameter of 700 μm and outer diameter of 1 mm. The air trapping cup was sealed with an approximately 500 μm layer of epoxy (Devcon, Inc.) and installed on the distal end of the fiber to have a gap between the fiber and the cup behind of the fiber.

In the micro-optic-based light delivery system, small optical parts such as micro-mirrors, micro-lenses, micro-prisms or combinations thereof can be used to redirect light. In this particular example, custom-made micro-mirrors were used as a micro-optics. The mirrors were fabricated by thermal evaporation of silver powder (part #303372-10G, Sigma-Aldrich, Inc.) on 2.5×3-mm pieces of 1-mm thick glass. The laser damage threshold for the mirrors was estimated to be 170 mJ/cm$^2$. No protective cup was used in the prototype.

Figure 3A:
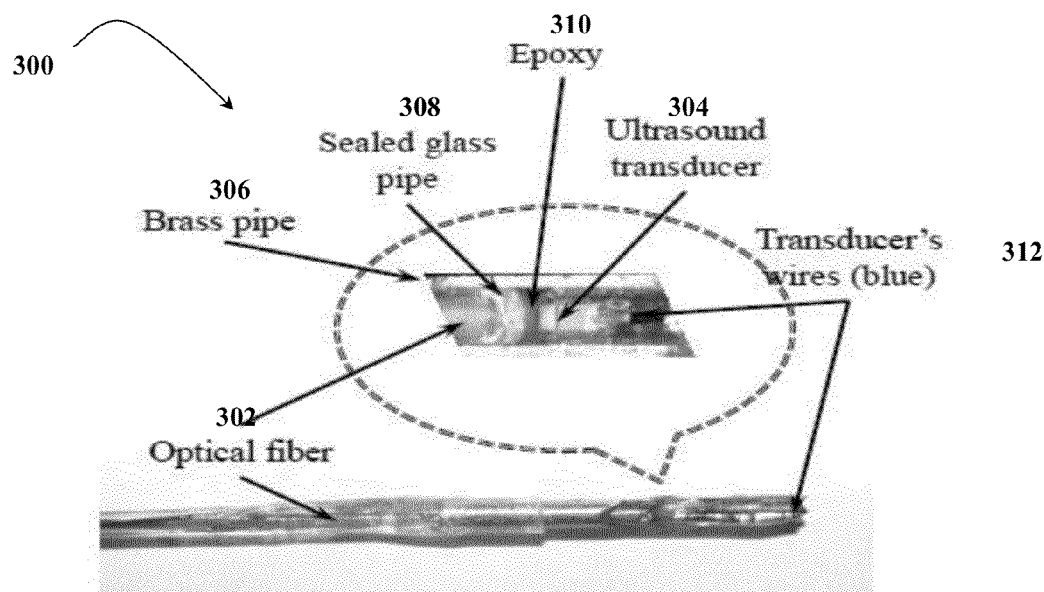
FIGS. 3A and 3B shows a distal end of a side fire fiber-based IVUS/IVPA imaging catheter capable of rotating inside a lumen.
Figure 3B:
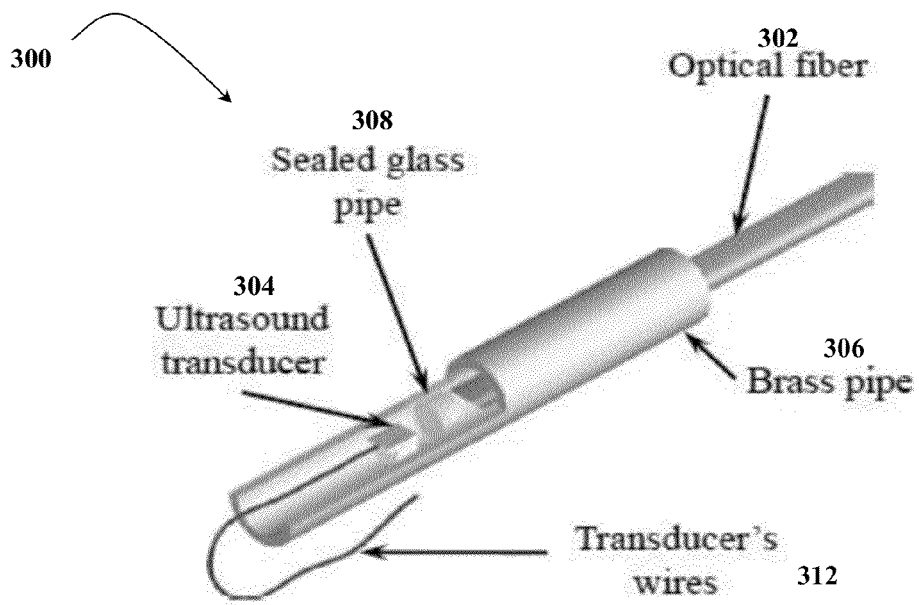

A photograph of an advanced prototype of the side fire fiber-based integrated IVUS/IVPA imaging catheter 300 utilizing a single-element ultrasound transducer 304 is shown in FIG. 3A. The optical fiber 302 with a core diameter of 600 μm and polyamide jacketing (Polymicro Technologies, Inc.) was polished at the angle of 35°. The gas trapping cup 308 with air inside was installed on the distal tip of the fiber. The PVDF-based unfocused ultrasound transducer 304 with the central frequency of 40 MHz capable of working in both ultrasound and photoacoustic modes is incorporated with the light delivery system 302 and 308 using a 10-mm long brass pipe 306 with inner and outer diameters of 1 and 1.5 mm and is connected with transducer wires 312. An epoxy 310 was utilized to fix together all parts. An assembly of the advanced integrated imaging catheter 300 is shown in details in FIG. 3B. Comparing with the previously described prototypes, such integrated IVUS/IVPA imaging catheter 300 is capable of imaging immobile tissues while the catheter itself is rotated inside a lumen.

Figure 4:
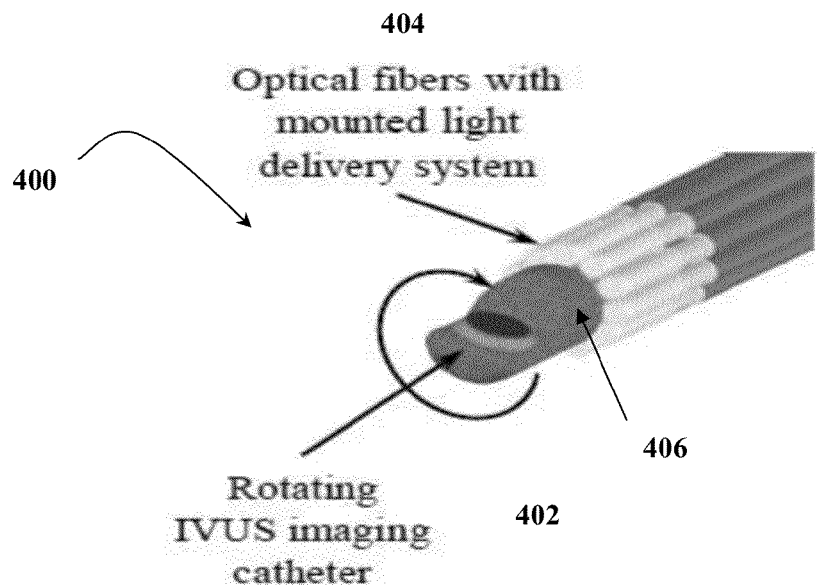
FIG. 4 demonstrates designs of a distal end of the integrated IVUS/IVPA imaging catheters—a schematic diagram demonstrating a design wherein an ultrasound unit is a single-element market-available intravascular ultrasound imaging catheter that rotates inside of a lumen while optical unit comprises several optical fibers with a light delivery system installed at each optical fiber. The light delivery system is stationary and irradiates a whole cross-section of an artery imaged by ultrasound imaging catheter.

Another possible design of the integrated IVUS/IVPA imaging catheter 400 based on the single element-based IVUS imaging catheter 402 is shown schematically in FIG. 4. In this design, the light delivery system is based on an optical fiber bundle 404 where the optical fibers of the bundle 404 are fixed a rigid cylinder 406 and distributed around the IVUS imaging catheter 402. Either side fire fiber-based or micro-optic-based light delivery system can be installed on the distal tips of each optical fiber 402. The side fire fiber or the micro-optic-based light delivery system directs light away from the ultrasound transducer. The IVUS imaging catheter 402 is rotating inside of this cylinder 406 while the cylinder 406 and fixed on it optical bundle 404 is immobile. Unlike the previously described prototypes, in this design, thinner optical fibers with diameters ranging from 50 μm provides the flexibility that makes the integrated IVUS/IVPA imaging catheter 400 suitable for in vivo imaging.

Figure 5A:
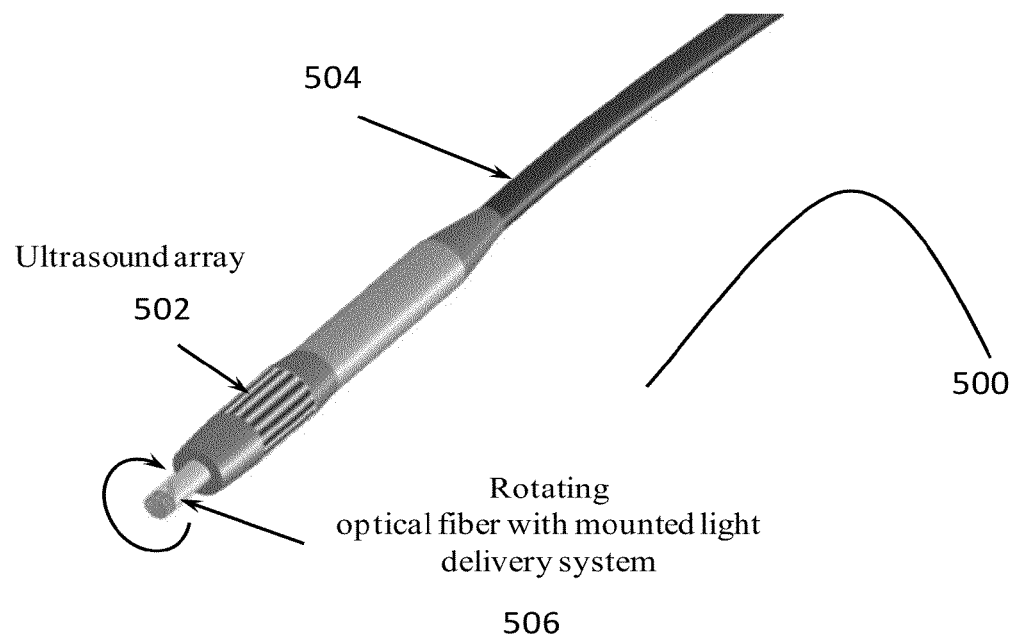

The schematic diagram design of an integrated IVUS/IVPA imaging catheter 500 based on an ultrasound imaging catheter 504 is shown in FIG. 5A. An ultrasound array 502 is utilized both to probe a tissue in pulse-echo mode and to detect photoacoustic transients generated into the tissue as a result of light-tissue interaction. The side fire fiber-based light delivery system is installed on a single optical fiber 506. The photograph of the prototype of the ultrasound array-based integrated IVUS/IVPA catheter 500 used in the studies is shown in FIG. 5B. The design utilizes the market-available ultrasound array 502 (Eagle Eye, Volcano, Inc.) with the central frequency of 20.75 MHz and the bandwidth of 40% and a single optical fiber 506 with a core diameter of 600 μm in Polyamide jacketing (Polymicro Technologies, Inc.). The mechanical rotation of the optical fiber 506 should be synchronized with the electronic rotation of ultrasound one emitted by the ultrasound array 502. The light delivery system is based on side fire fiber.

To test the invention, a point-target phantom 600 comprising of twelve graphite rods 602-624 was used. A photograph of a point-target phantom used in the studies and its structure are shown in FIGS. 6A and 6B, respectively. All twelve pencil rods 602-624 with diameter of 0.57±0.01 mm were oriented perpendicularly to an imaging cross-section 626. Eleven of them (602-622) were located spirally 4 to 9 mm away from the center of the phantom with 0.5 mm increment step. An inner diameter of a whole in the phantom is 6 mm. In addition, one rod 624 is located separately 10 mm away from the axis of the phantom.

A tissue-mimicking environment of the phantom to mimic artery's wall is not shown in FIGS. 6A and 6B was made out of 10% gelatin (Type A, Sigma-Aldrich, Inc.). Ultrasound properties were mimicked by silica particles (Sigma-Aldrich, Inc.) with 0.5% weight concentration and average size of 40 μm.[43] Optical scattering were mimicked by 20% of low fat milk (volume concentration).[44] The overall sizes of the phantom's body are measured to be 40×35×30 mm (L×W×H).

Figure 7:
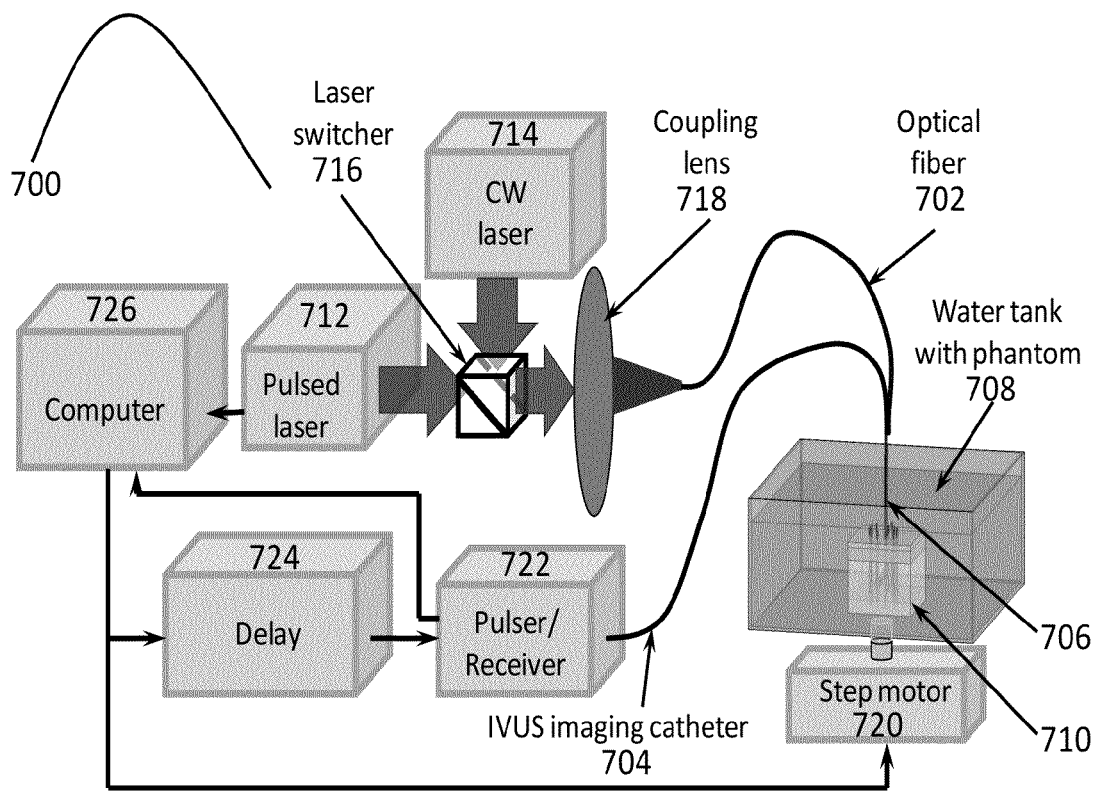
FIG. 7 shows a block diagram of the combined IVUS/IVPA imaging system operating with an integrated catheter.

The block diagram of the IVUS/IVPA and elasticity imaging and therapy system 700 is shown in FIG. 7 with optical fiber 702, coupling lens 718, a CW laser 714 and laser switcher 716. The distal end of the integrated catheter 706 was inserted into the lumen and placed at the center of the vessel-mimicking phantom 710. The proximal ends of the light delivery system incorporated longitudinally with the IVUS imaging catheter 704 were connected with the output of the laser source 712 and the ultrasound pulser/receiver 722, respectively (FIG. 7). The output of laser source 712 is also provided to laser switcher 716. The output of laser switcher 716 is provided to coupling lens 718 and optical fiber 702. Laser switcher 716 is operable to switch in CW laser 714 as the laser source. A tunable in near-infrared spectral region (680-960 nm and 1100-2400 nm) pulsed laser system 712 was used. Particularly, an OPO (Vibrant II, Opotek, Inc.) with pulse duration of 5 ns and repetition rate of 10 Hz was operated at 730 nm. To image phantom 710 without and with tissue-mimicking environment, the pulse energy measured on distal ends of both designs of light delivery systems comprised 1.4 mJ and 2.4 mJ respectively. The IVUS imaging catheter 704, used in both photoacoustic (echo only) and ultrasound (pulse-echo) modes, was operated by an ultrasound pulser/receiver 722 (5073PR, Panametrics-NDT, Inc.). Each radiofrequency (RF) signal consisted of photoacoustic and, delayed on 10 μs by a function generator 724 (33250A, Agilent, Inc.), ultrasound signatures. RF signals were captured by data acquisition card 726 (CompuScope 12200, GageScope, Inc.) and processed off-line.

The phantom was placed into a water tank 708 rotated precisely by a stepper motor 720 (ACCU Coder, Encoder Products, Inc.), while the integrated IVUS/IVPA imaging catheter 706 was fixed approximately on the axis of rotation to image point targets. One frame (360° rotation) included 251 A-lines. The averaging of 30 was applied to each A-line. RF signals were averaged, demodulated and scan converted to cover the 6.2-mm-radius field of view. No corrections or light fluency compensations were applied. Both designs of integrated IVUS/IVPA imaging catheters are capable of performing pullback 3-D imaging—a linear 1-D motion axis can be used to move the integrated catheter 706 relative to the phantom 710 thus allowing new cross-section to be imaged.

Figures 8A, 8B:
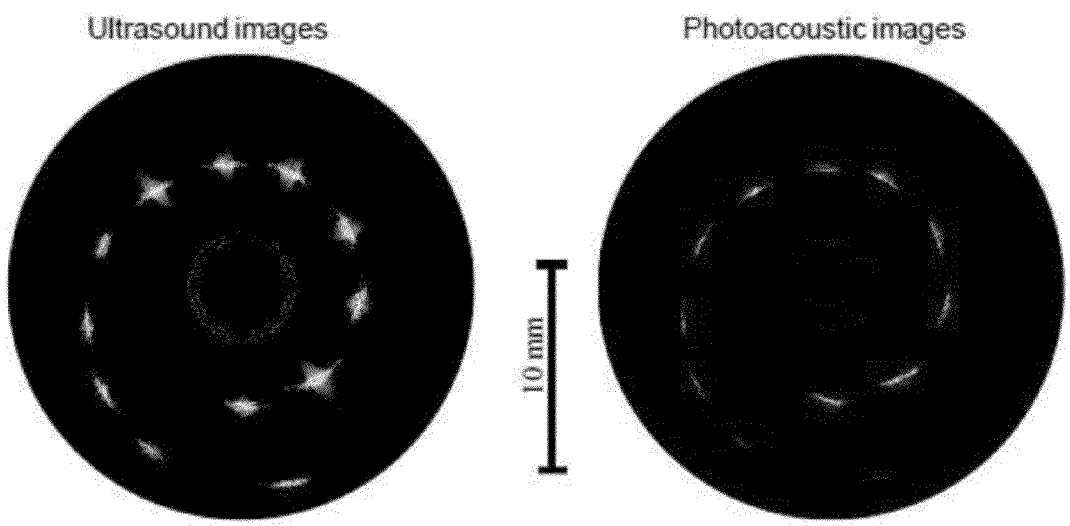
FIGS. 8A-8D show study images obtained by the side fire fiber- and mirror-based integrated IVUS/IVPA catheter.

In order to demonstrate that the invention may be used for combined IVUS/IVPA imaging, the prototypes of integrated IVUS/IVPA imaging catheters shown in FIGS. 1B, 2A, 3A, and 5B were initially tested in phantom studies. The ultrasound and photoacoustic images of the point-target phantom obtained by the side fire fiber-based catheter are displayed in FIG. 8A and FIG. 8B, respectively. All ultrasound and photoacoustic images are shown in the dynamic range of 29 dB and 25 dB respectively. The ultrasound B-scan in FIG. 8A shows the structure of the phantom where all twelve point targets are visible. The brightness of the targets slightly decreases with the depth due to attenuation of the high-frequency (40 MHz) ultrasound in water and a divergence of the ultrasound beam.

The photoacoustic image in FIG. 8B demonstrates a decrease of the photoacoustic signal strength with the depth due to the light distribution in the phantom. Indeed, the light divergence increases the area of illumination with the distance from the catheter and, therefore, decreases the fraction of the light absorbed by the targets located further away from the catheter.

Figures 8C, 8D:
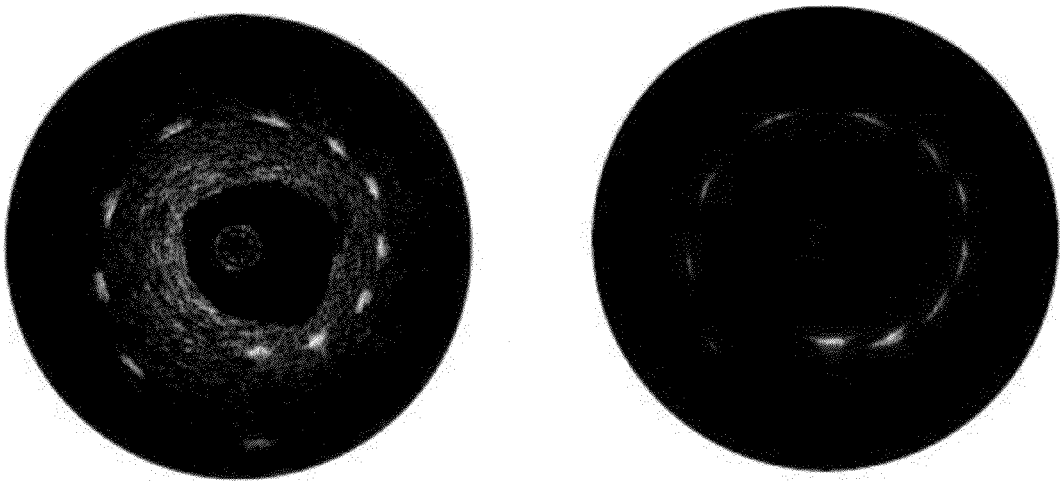

The ultrasound and photoacoustic B-scans of the point-target phantom within the tissue-mimicking environment are shown in FIGS. 8C and 8D, respectively. The ultrasound image in FIG. 8C exhibits the structure of the phantom. However, the decrease of the brightness of the targets with depth is greater than in FIG. 8A because ultrasound attenuation in tissue-mimicking environment is greater than that in water. This environment is not noticeable in the photoacoustic image in FIG. 8D due to modest light absorption in the gelatin and silica particles at 730 nm. However, the decrease of the photoacoustic transient magnitude from the targets in tissue-mimicking environment with the depth is greater than in water (FIG. 8B) because of the light scattering in the surrounding material. The light energy decays exponentially with the distance. The target that is further away from the catheter becomes invisible due to limited light energy reaches the target. Also, the generated photoacoustic wave attenuates as it travels to the transducer.

Figure 9A:
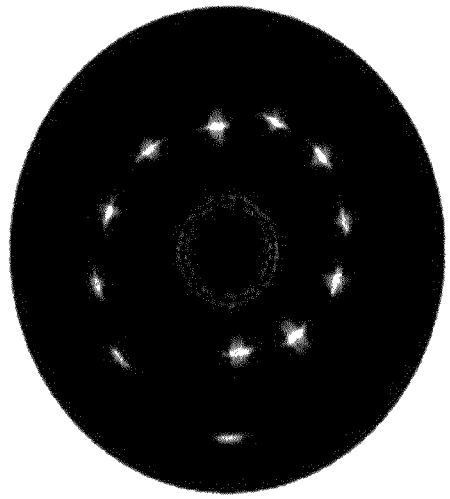
FIGS. 9A-9D show study images obtained by the side fire fiber- and mirror-based integrated IVUS/IVPA catheter.
Figure 9B:
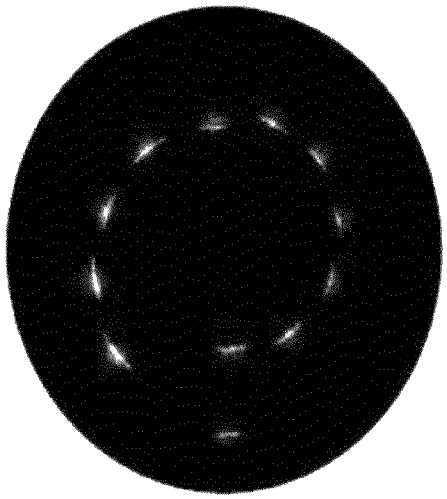

The ultrasound and photoacoustic B-scans of the point-target phantom obtained using the mirror-based catheter are shown in FIGS. 9A and 9B, respectively. All 12 targets are clearly indicated in FIG. 9A. Brightness of targets decreases slightly with depth.

The photoacoustic image in FIG. 9B indicates that the brightness of target points increases slightly for 1 through 7 targets (see FIG. 6B) because the closer point targets are not illuminated well while targets 8 through 11 were irradiated almost uniformly. Finally, the brightness of twelfth target is modest because this target is located too far from the catheter. There is a limited overlap between ultrasound and light beams.

Figure 9C:
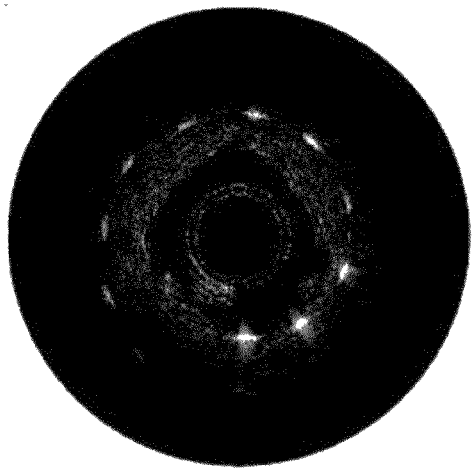
Figure 9D:
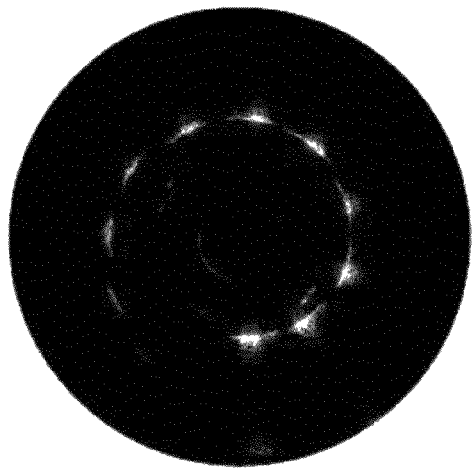

The ultrasound and photoacoustic images of the point targets in the tissue-mimicking environment are shown in FIGS. 9C and 9D, respectively. Similar to FIG. 9A, all targets are detected in FIG. 9C and, as expected, the brightness of targets decreases with a distance from the transducer.

The photoacoustic image in FIG. 9D indicates that targets located closer to the catheter generate greater photoacoustic transients due to strong light scattering in the background. Indeed, the directivity of the laser beam is affected by light scattering, so the absorbed light energy rapidly decreases with depth.

Figures 10A, 10B:
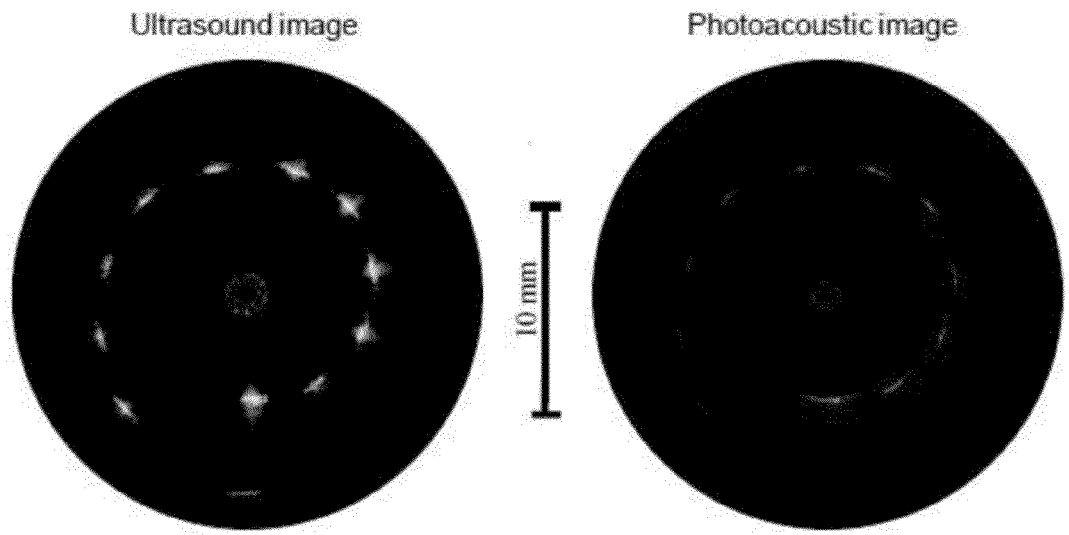
FIGS. 10A and 10B show study images obtained by the side fire fiber-integrated IVUS/IVPA catheter.

Under clinical condition, light scattering in blood adds to that in soft tissues in the near-infrared spectral region[45]. The whole blood in vessel was modeled by 20% solution of low-fat milk[46,47]. The ultrasound and photoacoustic images of the phantom obtained by side fire fiber-based imaging catheter are shown in FIGS. 10A and 10B, respectively. As expected, FIG. 10A shows all 12 target points and the decrease rate of the brightness of the targets with the depth is almost the same as it is shown in FIG. 8A in the ultrasound image of the phantom in water. However, the light scattering results in a significant exponential attenuation in the milk solution so that the brightness of target points shown in FIG. 10B decreases rapidly with the depth. Nevertheless, the photoacoustic transients generated by 1 through 6 targets are clearly detectable. These targets are located 4 to 6.5 mm away from the imaging catheter so that photoacoustic imaging of the artery's walls in the presence of blood is possible. In addition, the brightness of the targets can be increased by an elevating the light energy as it will be discussed herein below.

Figures 11A, 11B:
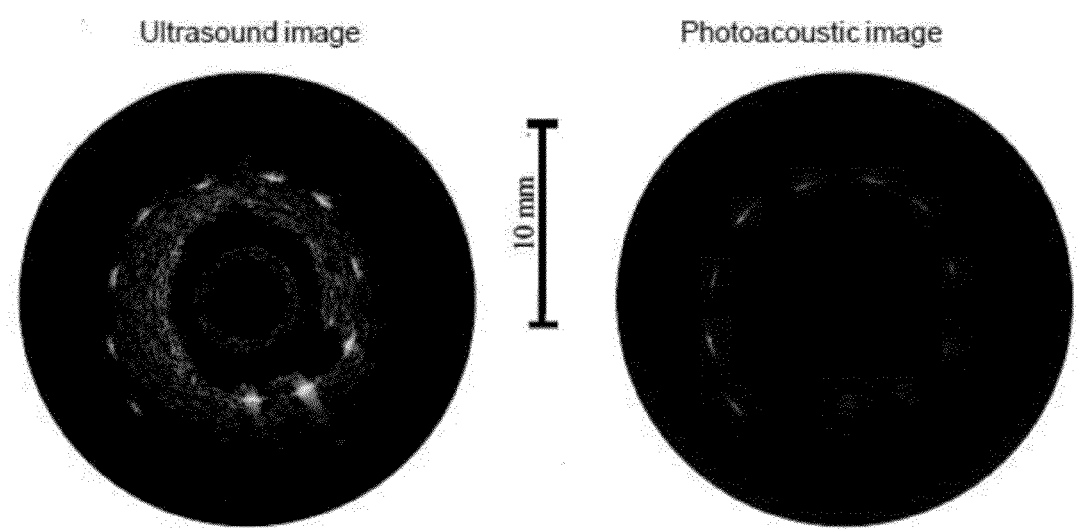
FIGS. 11A and 11B show study images obtained by the mirror-based integrated IVUS/IVPA catheter.

Due to the contrast between optical absorption coefficients of blood[48] and aorta tissue[49], the photoacoustic signal from the blood may dominate in photoacoustic signature at certain wavelengths. To avoid the possible saturation of photoacoustic signal from blood, both side-fiber and mirror-based light delivery designs of the integrated catheters can be refocused several millimeters further from the catheter. The ultrasound and photoacoustic images of the phantom in tissue-mimicking environment obtained by refocused mirror-based catheter are shown in FIGS. 11A and 11B, respectively in dynamic ranges of 29 and 25 dB respectively. The transducer was shifted two millimeters away from the mirror. The ultrasound images in FIG. 11A and FIG. 9C differ due to different imaged cross-sections only. However, such refocusing degrades a photoacoustic transient from rods located closer while farer rods appear brighter (FIG. 11B).

In order to demonstrate that the integrated IVUS/IVPA imaging catheter is capable of imaging blood vessels in vivo, the phantom shown in FIG. 6A was placed into tissue-mimicking environment and imaged using the catheter shown in FIG. 3A. FIG. 12A demonstrates the set-up 1200. The phantom 1202 was placed on one side of the water tank 1204 such that water filled the lumen 1208 where the catheter 1206 was inserted in. The ultrasound and photoacoustic images of the phantom are presented in FIGS. 12B and 12C, respectively. Comparing with results presented in FIGS. 8C and 8D, the geometry of the phantom is disfigured because of the catheter was not located on the axis of the phantom. However, the ultrasound image in FIG. 12B depicts clearly point targets and tissue-mimicking environment while the photoacoustic image in FIG. 12C identifies the areas with elevated optical absorption.

Figure 13A:
FIGS. 13A and 13B show study images obtained using the ultrasound array-based integrated IVUS/IVPA catheter with side fire fiber-based light delivery system (FIG. 5B)
Figure 13B:
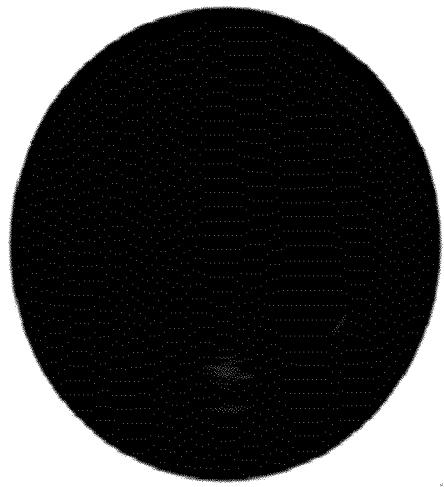

The ultrasound and photoacoustic B-scans of the point-target phantom obtained using the ultrasound array-based integrated IVUS/IVPA catheter with side fire fiber-based light delivery system are shown in FIGS. 13A and 13B, respectively. In this study the ultrasound array was stationary and ultrasound beam was electronically scanned. The optical fiber was also stationary directed and the rod 614 (see FIG. 6B). All 12 pencil rods are clearly indicated in FIG. 13A so the structure of the phantom is depicted clearly. Brightness of targets decreases slightly with depth but such significantly as in FIGS. 8A and 9A due to lower central frequency of the ultrasound array.

The photoacoustic image in FIG. 13B indicates the only one point source because the optical unit was not rotated. The mechanical rotation of the light delivery system is possible for sure as it is confirmed by results shown in FIGS. 12A and 12B.

While 2.5-mJ laser pulses were utilized for IVPA imaging of phantom placed in water, light absorption and light scattering in blood will attenuate the light energy thus making the photoacoustic imaging difficult. In addition, the optical absorption contrast between different tissue types may be limited[45]. All of these require relatively high laser fluence output from the integrated catheter. The optical parts such as optical fibers and micro-mirrors used currently in the invention limit the laser energy so 14 mJ maximum can be delivered now into lumen. However, the construction of the invention itself does not limit the laser energy that could be potentially delivered is the appropriate optical parts with higher light damage thresholds will be utilized. For example, the commercially available micro-mirrors have a laser damage threshold of 1 J/cm$^2$ while that of the material of optical fiber's core used in the invention comprises over 30 GW/cm$^2$. Obviously, that the increase of light damage threshold of all optical parts will allow to increase the delivered light energy and, therefore, the optical contrast and imaging depth of IVUS imaging.

While the length of an integrated IVUS/IVPA imaging catheter does not typically exceed few meters, the light is will not be attenuated too much while propagating through the optical fiber with a regular light attenuation of several dB/km. However, the light delivery system mounted on distal tips of the fibers will cause the light lose. In the case of mirror-based system, the overall losses are estimated to be approximately 1.7% while the overall losses in side fire fiber-based system are expected to be around 6.5%. The anti-reflection coating can decrease the losses. In the case of side fire fiber-based system, it was assumed that the polishing angle $\beta<\beta_0$. Otherwise, if the light losses are increased up to 100% (see Eqs. (4) and (5)).

As shown in FIG. 5B an ultrasound array-based integrated IVUS/IVPA imaging catheter could not redirect light at an angle greater than 90° in spite of the fact that the effect of total internal reflection utilized. This aspect could limit applicability of such type of light delivery system in the array-based catheters. In such a case, the micro-optic-based system is preferable. As it is demonstrated in FIGS. 9A-9D, the mirror-based and, generally speaking, micro-optic-based light delivery system can be successfully in ultrasound array-based device. Note, the light scattering in blood and blood vessel tissues will result in a light redistribution so the side fire fiber-based light delivery system could also be capable of irradiating of imaging cross-section with lower efficiency.

The possible design of proximal ends of the integrated IVUS/IVPA imaging catheters includes the stepped motor or the like to rotate the catheter around its axis. The two wires are flattened and attached either to the fiber or to the fiber bundle whatever is used to deliver light. An ultrasound transducer is attached as it is shown in the figures, so that the cross-section of the combined catheter is circular along its working length. The optical fiber with wires should be coated, and be even along the fiber jacketing. The ready fiber is coupled with the laser and rotated by a motor.

The laser safety standards determined by ANSI limit the maximum acceptable radiation fluence on skin from 20 mJ/cm$^2$ in visible spectral range to 100 mJ/cm$^2$ at 1050 nm.[50] However, these values do not apply to blood and inner soft tissues. It was reported[51] that the temperature increase in arterial tissues caused by laser pulse with fluence of 85 mJ/cm$^2$ comprises 5° C. and this value was considered as safe. The increase of blood temperature caused by a 2.4-mJ laser was estimated assuming the heat capacity and density of blood is equal to that of water. If the pulse is 2.7-times attenuated by blood at the distance equal to inversed extinction coefficient[52] and size of the outlet of light delivery system is 1 mm×1 mm then the increase of blood temperature is approximately 10° C. This value can be, however, decreased with the greater size of outlet. Therefore, the IVPA imaging can be thermally safe.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

WIPO Patent Application No. WO/2010/080776: Systems and Methods for Making and Using Intravascular Ultrasound Systems with Photo-Acoustic Imaging Capabilities.

U.S. Pat. No. 7,711,413: Catheter Imaging Probe and Method.

C. L. de Korte, M. J. Sierevogel, F. Mastik, C. Strijder, J. A. Schaar, E. Velema, G. Pasterkamp, P. W. Serruys and A. F. W. van der Steen, Circulation, 105, 1627-1630 (2002).

S. E. Nissen and P. Yock, Circulation, 103, 604-616 (2001).

S. P. Schwarzacher, P. J. Fitzgerald and P. G. Yock, Seminars in Interventional Cardiology 2, 1-9 (1997).

S. Sethuraman, S. R. Aglyamov, J. H. Amirian, R. Smalling and S. Y. Emelianov, IEEE Transactions on Ultrasonics, Ferroelectrics, and Frequency Control, 54, 978-986 (2007).

V. E. Gusev and A. A. Karabutov. Laser Optoacoustics, American Institute of Physics, New York; 1993.

C. K. N. Patel and A. C. Tam, Reviews of Modern Physics, 53, 517-550 (1981).

A. C. Tam, Reviews of Modern Physics, 58, 381-431 (1986).

L. Gao, K. J. Parker, R. M. Lerner and S. F. Levinson, Ultrasound in Medicine and Biology, 22, 959-977 (1996).

J. Ophir, S. K. Alam and B. S. Garra, Journal of Medical Ultrasonics, 29, 155-171 (2002).

J. Ophir, I. Cespedes, B. Garra, H. Ponnekanti, Y. Huang and N. Maklad, European Journal of Ultrasound, 3, 49-70 (1996).

K. J. Parker, L. Gao, R. M. Lerner and S. F. Levinson, IEEE Engineering in Medicine and Biology Magazine, 15, 52-59 (1996).

J. D'Hooge, A. Heimdal, F. Jamal and e. all, European Journal of Echocardiography, 1, 154-170 (2000).

C. L. de Korte, E. I. Cespedes, A. F. W. van der Steen, G. Pasterkamp and N. Bom, European Journal of Ultrasound, 7, 219-224 (1998).

K. W. Hollman, S. Y. Emelianov, J. H. Neiss and e. al., Cornea, 21, 68-73 (2002).

S. F. Levinson, M. Shinagawa and T. Sato, Journal of Biomechanics, 28, 1145-1154 (1995).

B. M. Shapo, J. R. Crowe, A. R. Skovoroda, K. J. Eberle, N. A. Cohn and M. O'Donnell, IEEE Transactions on Ultrasonics, Ferroelectrics, and Frequency Control, 43, 234-246 (1996).

J. Shah, S. R. Aglyamov, K. Sokolov, T. E. Milner and S. Y. Emelianov, Optics Express, 16, 3776-3785 (2008).

J. Shah, S. Park, S. r. Aglyamov, T. Larson, L. Ma, K. Sokolov, K. Johnston, Milner T. and S. Y. Emelianov, Proceedings of the 2008 SPIE Photonics West Symposium: Photons Plus Ultrasound: Imaging and Sensing, 6856, 68560U:1-7 (2008).

J. Shah, S. Park, S. R. Aglyamov, T. Larson, L. Ma, K. Sokolov, K. Johnston, T. E. Milner and S. Y. Emelianov, Journal of Biomedical Optics, 13, 034024 (2008).

J. Shah, S. Thompson, T. E. Milner and S. Y. Emelianov, Lasers in Surgery and Medicine 40, 680-687 (2008).

X. Jin, Y. Xu, L. V. Wang, Y. R. Fang, C. I. Zanelli and S. M. Howard, Medical Physics, 32, 5-11 (2004).

T. Long, V. Amin, S. McClure, R. Roberts, L. Wu, M. Heise and T. Ryken, Proceedings of the 2008 SPIE Photonics West Symposium: Photons Plus Ultrasound: Imaging and Sensing, 6513, (2007).

U. Utzinger and R. Richards-Kortum, Journal of Biomedical Optics, 8, 121-147 (2003).

S. R. Aglyamov, A. R. Skovoroda, H. Xie, K. Kim, J. M. Rubin, M. O'Donnell, T. W. Wakefield, D. Myers and S. Y. Emelianov, International Journal of Biomedical Imaging, 2007, 11 pages (2007).

J. Shah, A. B. Karpiouk and S. Y. Emelianov, Abstract and Presentation at the 2009 SPIE Photonics West Symposium: Photons Plus Ultrasound: Imaging and Sensing, (2009).

J. Shah, J. Mendeloff and S. Y. Emelianov, Abstract of the 25th Annual Houston Conference on Biomedical Engineering Research, The Houston Society for Engineering in Medicine and Biology, 53 (2008).

R. Virmani, F. D. Kolodgie, A. P. Burke, A. Farb and S. M. Schwartz, Arteriosclerosis, Thrombosis, and Vascular Biology, 20, 1262-1275 (2000).

M. Naghavi, P. Libby, E. Falk, S. W. Casscells, S. Litovsky, J. Rumberger, J. J. Badimon, C. Stefanadis, P. Moreno, G. Pasterkamp, Z. Fayad, P. H. Stone, S. Waxman, P. Raggi, M. Madjid, A. Zarrabi, A. Burke, C. Yuan, P. J. Fitzgerald, D. S. Siscovick, C. L. de Korte, M. Aikawa, K. E. J. Airaksinen, G. Assmann, C. R. Becker, J. H. Chesebro, A. Farb, Z. S. Galis, C. Jackson, I.-K. Jang, W. Koenig, R. A. Lodder, K. March, J. Demirovic, M. Navab, S. G. Priori, M. D. Rekhter, R. Bahr, S. M. Grundy, R. Mehran, A. Colombo, E. Boerwinkle, C. Ballantyne, J. Insull, W., R. S. Schwartz, R. Vogel, P. W. Serruys, G. K. Hansson, D. P. Faxon, S. Kaul, H. Drexler, P. Greenland, J. E. Muller, R. Virmani, P. M. Ridker, D. P. Zipes, P. K. Shah and J. T. Willerson, Circulation, 108, 1664-1672 (2003).

H. C. Stary, A. B. Chandler and R. E. Dinsmore, Arteriosclerosis, Thrombosis, and Vascular Biology 15, 1512-1531 (1995).

P. C. Beard and T. N. Mills, Physics in Medicine and Biology, 42, 177-198 (1997).

A. Berlis, H. Lutsep, S. Barnwell, A. Norbash, L. Wechsler, C. A. Jungreis, A. Woolfenden, G. Redekop, M. Hartmann and M. Schumacher, Stroke, 35, 1112-1116 (2004).

P. M. Henrichs, J. W. Meador, J. M. Fuqua and A. A. Oraevsky, Proceedings of SPIE, 5697, 217-223 (2005).

Y. Y. Petrov, I. Y. Petrova, I. A. Patrikeev, R. 0. Esenaliev and D. S. Prough, Optics Letters, 31, 1827-1829 (2006).

M. C. Pilatou, N. J. Voogd, F. F. M. de Mul, W. Steenbergena and L. N. A. van Adrichem, Review of Scientific Instruments, 74, 4495-4499 (2003).

H. F. Zhang, K. Maslov, M. Sivaramakrishnan, G. Stoica and L. V. Wang, Applied Physics Letters, 90, 053901 (2007).

S. Sethuraman, J. H. Amirian, S. H. Litovsky, R. Smalling and S. Y. Emelianov, Optics Express, 15, 16657-16666 (2007).

S. Sethuraman, J. H. Amirian, S. H. Litovsky, R. Smalling and S. Y. Emelianov, Optics Express, 16, 3362-3367 (2008).

Boston Scientific Inc. Atlantis RS Pro imaging Catheter. See at http://www.bostonscientific.com Volcano Corporation Inc. Visions® PV8.2F imaging catheter. See at http://www.volcanocorp.com.

P. C. Beard, F. Perennes, E. Draguioti and T. N. Mills, Optics letters, 23, 1235-1237 (1998).

P. A. Fomitchov, A. K. Kromine and S. Krishnaswamy, Applied Optics, 41, 4451-4459 (2002).

J. G. Fujimoto, S. A. Boppart, G. J. Tearney, B. E. Bouma, C. Pitris and M. E. Brezinski, Heart, 82, 128-133 (1999).

E. L. Madsen, J. A. Zagrebski, M. C. MacDonald and G. R. Frank, American Association of Physical Medicine, 18, 1171-1181 (1991).

M. D. Waterworth, B. J. Tarte, A. J. Joblin, T. van Doom and H. E. Niesler, Australasian Physical and Engineering Sciences in Medicine 18, 39-44 (1995).

W.-F. Cheong, S. A. Prahl and A. J. Welch, IEEE Journal of Quantum Electronics, 26, 2166-2185 (1990).

G. Mitic, J. Kolzel, J. Otto, E. Plies, G. Solkner and W. Zinth, Applied Optics, 33, 6699-6710 (1994).

B. W. Pogue and M. S. Patterson, Journal of Biomedical Optics, 11, 041102 (2006).

S. Prahl, Oregon Medical Laser Center, http://omlc.ogi.edu/spectra/hemoglobin/summary.html, (2000).

J. M. C. van Gemert, R. M. Verdaasdonk, E. G. Stassen and G. Schets, Lasers in Surgery and Medicine, 5, 235-262 (1985).

ANSI. American national standards for Safe Use of Lasers. Volume 2136.1-2000. New York, USA: American National Standards Institute; 2000.

S. Sethuraman, S. R. Aglyamiv, R. W. Smalling and S. Y. Emelianov, Ultrasound in Medicine and Biology, 34, 299-308 (2008).

D. J. Faber, M. C. G. Aalders, E. G. Mik, B. A. Hooper, M. J. C. van Gemert and T. G. van Leeuwen, Physical Review Letters, 93, 028102 (2004).

What is claimed is:

1. An intravascular ultrasound and photoacoustic imaging and therapeutic device comprising:

a catheter with a proximal end and a distal end;

one or more intravascular ultrasound imaging and therapeutic units comprising a proximal end and a distal end, wherein the distal end comprises one or more single-element ultrasound transducers, one or more ultrasound arrays or a combinations thereof, wherein the proximal end comprises a port connecting the one or more ultrasound units to one or more ultrasound pulser-receivers;

one or more optical units comprising a proximal end and a distal end combination, wherein the distal end comprises one or more optical fibers, one or more optical bundles or a combination of both and one or more light delivery systems comprising micro-optics mounted on one or more optical fibers or one or more optical bundles or based on total internal reflection of the optical fiber, wherein the proximal end comprises a port to couple at least one optical unit to at least one of a pulsed light source or a continuous wave (CW) light source, wherein:

the distal end of the ultrasound and optical units are aligned such that ultrasound and optical waves are directed to a target tissue;

the ultrasound waves are directed to a first region of the target tissue;

the optical waves are directed to a second region of the target tissue; and the first region and the second region are simultaneously overlapping;

an ultrasound pulser-receiver connected to the proximal end of the one or more ultrasound imaging and therapeutic units;

a light source connected to the proximal end of the one or more optical units comprising one of a pulsed light source having a pulsed laser fluence and a CW light source having a CW laser fluence; and an imager connected to the proximal end of the catheter, to the pulser-receiver and to pulsed light source to capture one or more ultrasound, photoacoustic and elasticity images, wherein a majority of a laser and ultrasound energy is uni-directionally directed at the target tissue and the imager is capable of a reconstruction of a distribution of an ultrasound impedance, a shear elastic modulus and an absorbing tissues deposition in an imaged target tissue cross-section and of performing an optical therapy, an acoustic therapy or both.

2. The device of claim 1, wherein the one or more optical units are incorporated longitudinally in or about the catheter.

3. The device of claim 1, wherein the one or more ultrasound units are incorporated longitudinally in or about the catheter.

4. The device of claim 1, wherein the ultrasound imaging and therapeutic unit comprises one or more single-element ultrasound transducers, an ultrasound transducer array or a combination thereof.

5. The device of claim 1, wherein the one or more ultrasound imaging and therapeutic units may rotate around a longitudinal axis of the catheter.

6. The device of claim 1, wherein at least one ultrasound imaging and therapeutic unit is capable of transmitting an ultrasound wave about the distal end of the catheter.

7. The device of claim 1, wherein the one or more ultrasound imaging and therapeutic units can irradiate an artery with short pulses of ultrasound waves with consequent detection of the reflected and scattered ultrasound waves in a tissue.

8. The device of claim 1, wherein the one or more ultrasound and therapeutic units is capable of detecting ultrasound waves generated in the target tissues as a result of a thermal expansion of the target tissues due to a heating by the pulsed laser light.

9. The device of claim 1, wherein a central frequency of one or more ultrasound imaging and therapeutic units is chosen to provide a required resolution and a penetration depth to image the artery and nearby tissues and plaques.

10. The device of claim 9, wherein the central frequency of one or more ultrasound imaging and therapeutic units is chosen to provide an ultrasound wave capable of performing a therapy.

11. The device of claim 1, wherein the one or more ultrasound imaging and therapeutic units can irradiate the artery with a long pulse or a CW ultrasound wave to provide a therapeutic effect.

12. The device of claim 11, wherein the one or more ultrasound imaging and therapeutic units can provide pulses of ultrasound waves with a duration in a range of 1 ns through 1 μs with a consequent detection of the ultrasound waves reflected in the tissues, scattered in the tissues or both.

13. The device of claim 11, wherein the duration of the pulses and a duty cycle of ultrasound waves may be varied as required for acoustic therapy.

14. The device of claim 1, wherein the one or more optical units comprise one or more optical fibers, multimode optical fibers, a fiber bundle or a combination thereof.

15. The device of claim 1, wherein the one or more optical units based on a single optical fiber, optical bundle or a combination thereof may rotate around a longitudinal axis of the catheter.

16. The device of claim 1, wherein the one or more optical fibers, the fiber bundle or the combination illuminates an area about the distal end of the catheter such that exposed area overlaps with the area where ultrasound waves are by the one or more ultrasound imaging and therapeutic units.

17. The device of claim 1, wherein a light delivery system is mounted on the distal end of the one or more optical fibers or optical bundles or combination thereof.

18. The device of claim 17, wherein the light delivery system utilizes a total internal reflection mechanism to overlap light and ultrasound waves.

19. The device of claim 17, wherein the micro-optics is attached to the distal end of the one or more optical units and aligned to the overlapping light and ultrasound waves.

20. The device of claim 1, wherein the proximal end of the one or more optical fibers or the fiber bundles comprises a polished tip, wherein the tip is designed to be coupled with a light source.

21. The device of claim 1, wherein an optically transparent tube with a sealed distal end is mounted hermetically on the distal end of the one or more optical units to maintain the total internal reflection.

22. The device of claim 21, wherein the tube in a side fire fiber-based design traps a gas while the proximal end of the tube is mounted on the distal end of the one or more optical units.

23. The device of claim 21, wherein the optically transparent tube is mounted on the distal end of the one or more optical units to protect the light delivery system and a patient.

24. The device of claim 21, wherein the tube in a micro-optics-based design is filled with a medium to decrease light losses.

25. The device of claim 1, wherein the distal end of one or more optical units in a side fire fiber-based design is polished at a certain angle to redirect light at almost near-right angles relative to the longitudinal axis of the catheter to perform a total internal reflection.

26. The device of claim 1, wherein the distal end of one or more optical units in the micro-optics-based design is equipped by micro-mirror, micro-lens, micro-prism, alone or in any combination thereof to redirect light at almost near-right angles relative to the longitudinal axis of the catheter.

27. The device of claim 1, wherein one or more optical units emits short pulsed light with a high fluence to perform a photoacoustic imaging.

28. The device of claim 1, wherein one or more optical units are capable of transmitting the CW or the long-pulse radiation to perform a light therapy.

29. The device of claim 1, wherein the pulser-receiver is capable of providing short ultrasound pulses with a consequent detection of scattered and reflected ultrasound waves in the target tissue, of providing long ultrasound pulses to perform acoustic therapy, and of detecting ultrasound waves generated in the target tissue as a result of the thermal expansion of an irradiated volume or combinations thereof.

30. The device of claim 1, wherein the pulsed laser is coupled with the proximal end of one or more optical units to irradiate the target tissue at one or more wavelengths.

31. The device of claim 30, wherein the wavelengths of electromagnetic radiation are chosen to provide the best optical contrast.

32. The device of claim 1, wherein the CW, the long-pulsed laser or both are coupled with proximal end of the one or more optical units to irradiate target tissues at one or more wavelengths.

33. The device of claim 32, wherein the wavelengths of CW electromagnetic radiation are chosen to provide optimal optical imaging and therapeutic effect.

34. The device of claim 1, wherein the imager is capable of at least one of: providing the reconstructed distributions of ultrasound impedances, an absorbing tissue deposition and shear elastic modulus and instructing a user to perform an acoustic therapy an optical therapy or both.

35. The device of claim 1, wherein the one or more optical light sources are coupled to the proximal end of one or more optical units through a laser switcher to allow irradiating at least one of a tissue by pulsed radiation, or a CW radiation.

36. A method of imaging and treating a target tissue in a subject comprising the steps of:
identifying a subject in need of treatment of a target tissue using an intravascular imaging and therapeutic device capable of combined intravascular ultrasound, photoacoustic, and elasticity imaging;
irradiating the target tissue with radiation, ultrasound energy, or both from an intravascular imaging and therapeutic device comprising:
a catheter with a proximal end and a distal end;
one or more intravascular ultrasound imaging and therapeutic units comprising a proximal end and a distal end, wherein the distal end comprises one or more single-element ultrasound transducers, one or more ultrasound arrays or a combinations thereof, wherein the proximal end comprises a port connecting the one or more ultrasound unit to a pulser-receiver;
one or more optical units comprising a proximal end and a distal end combination, wherein the distal end comprises one or more optical fibers, one or more optical bundles or a combination of both and one or more light delivery systems comprising micro-optics mounted on one or more optical fibers or one or more optical bundles or based on total internal reflection or both, wherein the proximal end comprises a port to couple at least one optical unit to at least one of a pulsed light source, wherein:
the distal end of the ultrasound and optical units are aligned such that ultrasound and optical waves are directed to the target tissue;
the ultrasound waves are directed to a first region of the target tissue;
the optical waves are directed to a second region of the target tissue; and
the first region and the second region are simultaneously overlapping;
a pulser-receiver connected to the proximal end of the one or more ultrasound imaging and therapeutic units;
a light source connected to the proximal end of the one or more optical units comprising one of a pulsed light source having a pulsed laser fluence, a CW or a long-pulse light source having a laser fluence; and
an imager connected to the proximal end of catheter, to pulser-receiver and to the pulsed light source to capture ultrasound, and photoacoustic signals with respect of their temporal appearance with consequent real-time or off-line reconstruction of one or more ultrasound, photoacoustic and elasticity images;
reconstructing a distribution of an ultrasound impedance, a distribution of a shear elastic modulus and a distribution of an a distribution of an absorbing or tissue deposition in an imaged tissue cross-section or a combination of thereof;
performing an acoustic therapy, a radiation therapy, or both of the target tissues; and
performing the imaging and therapy together or separate.

37. The method of claim 36, wherein the distribution of the ultrasound impedance is reconstructed by transmitting of short ultrasound waves into the target tissue with consequent detection of reflected ultrasound waves, scattered ultrasound waves or both.

38. The method of claim 36, wherein the distribution of the optical absorption is reconstructed by transmitting of short light pulses into the target tissue with a consequent detection of ultrasound waves generated in the tissue due to thermal expansion of the tissue due to absorbed light energy.

39. The method of claim 36, wherein the distribution of shear elastic modulus is reconstructed by collecting of ultrasound images of the same cross-section of an imaged blood vessel where one or more strain tensor components are measured assessing a local tissue's displacement in response to an external or a cardiac loading.

40. The method of claim 36, wherein the one or more ultrasound units irradiate an artery with long ultrasound pulses or CW ultrasound waves to perform an acoustic therapy of the artery.

41. The method of claim 36, wherein the one or more optical units can irradiate tissues by CW or long-pulse light to perform an optical therapy.

42. The method of claim 36, wherein the optical and the acoustic therapy can be performed either simultaneously or separately.

43. The method of claim 36, wherein the reconstruction of the distributions and therapy can be performed either simultaneously or consequently in any combinations.

44. The method of claim 36, wherein the imager is capable of providing imaging results or therapy results in a format determined by a user.

* * * * *

UNITED STATES PATENT AND TRADEMARK OFFICE
CERTIFICATE OF CORRECTION

PATENT NO. : 8,932,223 B2
APPLICATION NO. : 13/505345
DATED : January 13, 2015
INVENTOR(S) : Stanislov Emelianov, Andrei Karpiouk and Bo Wang It is certified that error appears in the above-identified patent and that said Letters Patent is hereby corrected as shown below:

In the Specification

In column 1, after the Title at line 5, please insert --STATEMENT OF FEDERALLY FUNDED RESEARCH This invention was made with government support under Grant no. R21 HL084076 awarded by National Institutes of Health. The government has certain rights in the invention.--.

Signed and Sealed this
Second Day of June, 2015

Michelle K. Lee
*Director of the United States Patent and Trademark Office*